(12) United States Patent
Han et al.

(10) Patent No.: US 6,207,697 B1
(45) Date of Patent: Mar. 27, 2001

(54) BENZIMIDAZOLINONES, BENZOXAZOLINONES, BENZOPIPERAZINONES, INDANONES, AND DERIVATIVES THEREOF AS INHIBITORS OF FACTOR XA

(75) Inventors: Qi Han, Wilmington, DE (US); Celia Dominguez, Westlake Village, CA (US); Eugene C. Amparo, Downington, PA (US); Jeongsook M. Park, Bear, DE (US); Mimi L. Quan, Newark, DE (US); Karen A. Rossi, Newark, DE (US)

(73) Assignee: DuPont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/149,826

(22) Filed: Sep. 8, 1998

Related U.S. Application Data

(60) Provisional application No. 60/058,288, filed on Sep. 9, 1997.

(51) Int. Cl.$^7$ .................. C07D 209/34; A61K 31/404; A61K 31/405
(52) U.S. Cl. .................. 514/409; 514/418; 548/409; 548/410; 548/486; 548/487
(58) Field of Search .................. 548/409, 410, 548/486, 487; 514/409, 418

(56) References Cited

U.S. PATENT DOCUMENTS

| | | | |
|---|---|---|---|
| 4,110,465 | * 8/1978 | Holmes | 424/274 |
| 4,985,448 | * 1/1991 | Zilch et al. | 514/339 |
| 5,317,103 | 5/1994 | Baker et al. | 544/367 |
| 5,886,191 | * 3/1999 | Dominguez et al. | 548/491 |
| 5,998,463 | * 12/1999 | Hulin et al. | 514/418 |

FOREIGN PATENT DOCUMENTS

| | | |
|---|---|---|
| 0540051 | 5/1993 | (EP) . |
| 0787727 | 8/1997 | (EP) . |
| 6227971 | 8/1994 | (JP) . |
| 9402477 | 2/1994 | (WO) . |

OTHER PUBLICATIONS

Gruda, Chemical Abstract No. 68:114341, 1968.*
Bolotov et al., Chemical Abstract No. 86:121089, 1977.*
Hoelck et al., Chemical Abstract No. 104:207267, 1986.*

* cited by examiner

Primary Examiner—Mukund J. Shah
Assistant Examiner—Deepak R. Rao
(74) Attorney, Agent, or Firm—David H. Vance

(57) ABSTRACT

The present application describes inhibitors of factor Xa of formula I:

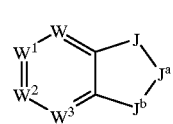

or pharmaceutically acceptable salt forms thereof, wherein W, $W^1$, $W^2$, and $W^3$ may be N or C and J, $J^a$, and $J^b$ combine to form a substituted carbocycle or heterocycle.

15 Claims, No Drawings

BENZIMIDAZOLINONES, BENZOXAZOLINONES, BENZOPIPERAZINONES, INDANONES, AND DERIVATIVES THEREOF AS INHIBITORS OF FACTOR XA

This application claims the benefit of U.S. Provisional Application Ser. No. 60/058,288, filed Sep. 9, 1997.

FIELD OF THE INVENTION

This invention relates generally to novel benzimidazolinones, benzoxazolinones, benzopiperazinones, indanones, and derivatives thereof as inhibitors of factor Xa, pharmaceutical compositions containing the same, and methods of using the same as anticoagulant agents for treatment and prevention of thromboembolic disorders.

BACKGROUND OF THE INVENTION

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: *Optimization of conditions for the catalytic effect of the factor IXa-factor VIII Complex: Probable role of the complex in the amplification of blood coagulation. Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

EP 0,540,051 and JP 06227971 describe a series of compounds useful as factor Xa inhibitors or to treat influenza based on the formula:

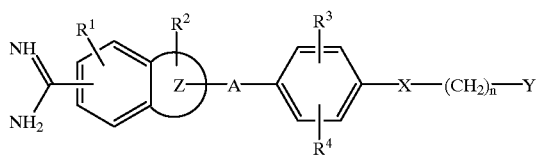

wherein A is an alkylene linker optionally substituted X is a bond, O, S, or carbonyl, n is 0–4, and Y is an optionally substituted carbocycle or heterocycle. The core ring containing Z can be a variety of benzofused heterocycles. However, the present invention does not involve compounds containing these benzofused heterocycles- Baker et al, in U.S. Pat. No. 5,317,103, discuss 5-$HT_1$ agonists which are indole substituted five-membered heteroaromatic compounds of the formula:

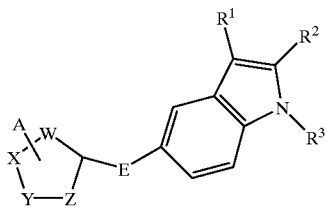

wherein $R^1$ may be pyrrolidine or piperidine and A may be a basic group including amino and amidino. Baker et al, however, do not appear to describe heterocycles which are part of the present invention.

Baker et al, in WO 94/02477, discuss 5-$HT_1$ agonists which are imidazoles, triazoles, or tetrazoles of the formula:

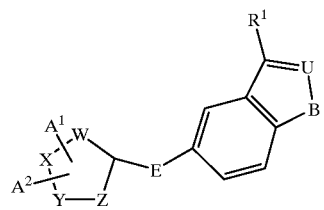

wherein $R^1$ represents a nitrogen containing ring system or a nitrogen substituted cyclobutane, and A may be a basic group including amino and amidino. But, the presently claimed invention doesn't relate to the heterocyclic cores of Baker et al.

EP 787,727 illustrates benzyl-thiazolidin-2,4-diones of the formula:

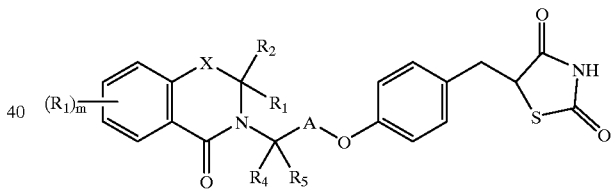

which are useful as hypoglycemic agents. However, these type of compounds are outside of the present Xa inhibitors.

SUMMARY OF THE INVENTION

Accordingly, one object of the present invention is to provide novel inhibitors of factor Xa or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors, discovery that compounds of formula (I):

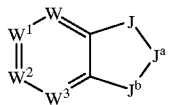

or pharmaceutically acceptable salt forms thereof, wherein W, $W^1$, $W^2$, $W^3$, J, $J^a$, and $J^b$ are defined below, are effective factor Xa inhibitors.

DETAILED DESCRIPTION OF PREFERRED EMBODIMENTS

[1] Thus, in a first embodiment, the present invention provides a novel compound of formula I:

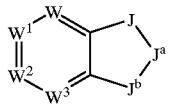

or stereoisomer or pharmaceutically acceptable salt thereof, wherein;
one of W, $W^1$, $W^2$, and $W^3$ is C—D and the remaining are C—$R^1$;
alternatively, W–$W^1$, $W^1$–$W^2$, or $W^2$–$W^3$ combine to form C($D^a$)N and the remaining are C—$R^1$;
D is selected from CN, C(=$NR^7$)$NR^8R^9$, NHC(=$NR^7$) $NR^8R^9$, $NR^8$CH(=$NR^7$), C(O)$NR^8R^9$, and $(CH_2)_t$ $NR^8R^9$;
$D^a$ is $NH_2$, NH($C_{1-3}$ alkyl), N($C_{1-3}$ alkyl)$_2$, or $C_{1-3}$ alkoxy;
J is selected from N(Z—A—B) and CR(Z—A—B); and
$J^a$ and $J^b$ together are selected from CONHCR$^e$R$^f$, SO$_2$NHCR$^e$R$^f$, (CR$^a$R$^b$)$_b$SO$_2$NR$^d$, and (CR$^a$R$^b$)$_b$COCO (CR$^e$R$^f$)$_c$, wherein b+c=0 or 1;
alternatively, J and $J^a$ together are selected from CON(Z—A—B) (CR$^e$R$^b$)$_q$ and N(Z—A—B)Q(R$^e$R$^b$)$_a$; and
$J^b$ is selected from NR$^d$, O, and CR$^e$R$^f$;
Q is CO or CS;
alternatively, J, $J^a$ and $J^b$ together are selected from CR(Z—A—B) (CR$^a$R$^b$)$_a$QNR$^d$, CR(Z—A—B) (CR$^a$R$^b$)$_d$C(O)O, CR(Z—A—B) NHCOCR$^e$R$^f$, CR(Z—A—B) NHSO$_2$CR$^e$R$^f$, N(Z—A—B)(CR$^a$R$^b$)$_a$QNR$^d$, N(Z—A—B)(CR$^a$R$^b$) C(O)O, N(Z—A—B) SO$_2$(CR$^e$R$^b$)$_a$CR$^e$R$^f$, N(Z—A—B) SO$_2$(CR$^a$R$^b$)$_a$NR$^d$, CON(Z—A—B)CR$^e$R$^f$, CONR$^b$(CR$^e$R$^f$)$_a$N(Z—A—B),

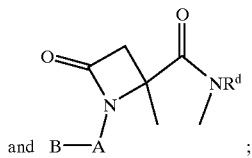

and B—A ;

R is selected from H, $C_{1-6}$ alkyl, $NH_2$, NH($C_{1-6}$ alkyl), N($C_{1-6}$ alkyl)$_2$, OH, $C_{1-6}$ alkoxy, $C_{1-6}$ alkoxy-$C_{1-4}$ alkyl, $(CH_2)_rNR^8R^9$, 5–6 membered aromatic heterocyclyl-$C_{1-4}$ alkyl, and aryl-$C_{1-4}$ alkyl, wherein the aromatic heterocyclyl and aryl groups are substituted with 0–1 $R^4$;
$R^a$ is selected from H, $C_{1-6}$ alkyl, C(O)$R^{2b}$, 5–6 membered aromatic heterocyclyl-$C_{1-4}$ alkyl, and aryl-$C_{1-4}$ alkyl, wherein the aromatic hetercyclyl and aryl groups are substituted with 0–1 $R^4$;

$R^b$ is H or $C_{1-2}$ alkyl;
$R^c$ is selected from H, $C_{1-6}$ alkyl, C(O)$R^{2b}$, S(O)$_pR^{2b}$, $BO_2H_2$, 5–6 membered aromatic heterocyclyl-$C_{1-4}$ alkyl, and aryl-$C_{1-4}$ alkyl, wherein the aromatic hetercyclyl and aryl groups are substituted with 0–1 $R^4$;
$R^d$ is selected from H, OH, $NH_2$, $C_{1-2}$ alkyl, and $C_{1-2}$ alkyl-OH,
alternatively, $R^c$ and $R^d$, when attached to adjacent atoms, together form a double bond;
$R^e$ is selected from H, OH, $NH_2$, $C_{1-2}$ alkyl, and $C_{1-2}$ alkyl-OH,
alternatively, $R^c$ and $R^e$, when attached to adjacent atoms, together form a double bond;
$R^f$ is H or $C_{1-2}$ alkyl;
Z is selected from a bond, $C_{1-4}$ alkylene, $(CH_2)_rO(CH_2)_r$, $(CH_2)_rNR^3(CH_2)_r$, $(CH_2)_rC(O)(CH_2)_r$, $(CH_2)_rC(O)(CH_2)_r$, $(CH_2)_rOC(O)(CH_2)_r$, $(CH_2)_rC(O)NR^3(CH_2)_r$, $(CH_2)_rNR^3C(O)(CH_2)_r$, $(CH_2)_rOC(O)O(CH_2)_r$, $(CH_2)_rOC(O) NR^3(CH_2)_r$, $(CH_2)_rNR^3C(O) O(CH_2)_r$, $(CH_2)_r NR^3C(O)NR^3(CH_2)_r$, $(CH_2)_rS(O)_p(CH_2)_r$, $(CH_2)_r SO_2NR^3(CH_2)_r$, $(CH_2)_rNR^3 SO_2(CH_2)_r$, and $(CH_2)_r NR^3SO_2NR^3(CH_2)_r$, provided that Z does not form a N—N, N—O, N—S, $NCH_2N$, $NCH_2O$, or $NCH_2S$ bond with the groups to which it is attached;
$R^1$, at each occurrence, is selected from H, F, Cl, Br, I, $(CF_2)_rCF_3$, $OR^2$, $NR^2R^{2a}$, $C(O)R^{2b}$, $(CF_2)_rCO_2R^2$, $S(O)_2 R^{2b}$, $NR^2C(O)R^{2b}$, $C(O)NR^2R^{2a}$, $SO_2NR^2R^{2a}$, $C_{3-6}$ carbocyclic residue substituted with 0–2 $R^4$, and 5–10 membered heterocyclic system containing from 1–4 heteroatoms selected from the group consisting of N, O, and S and substituted with 0–2 $R^4$;
$R^{1'}$, at each occurrence, is selected from H, $C_{1-3}$ alkyl, F, Cl, Br, I, —CN, —CHO, $(CF_2)_rCF_3$, $(CH_2)_rOR^2C$ $NR^2R^{2a}$, $C(O)R^{2c}$, $OC(O)R^2$, $(CF_2)_rCO_2R^2C$, $S(O)_pR^{2b}$, $NR^2$ $(CH_2)_rOR^2$, CH(=$NR^2C$)$NR^2R^{2a}$, $NR^2C(O)R^{2b}$, $NR^2C (O)NHR^{2b}$, $NR^2C(O)_2R^{2a}$, $OC(O)NR^{2a}R^{2b}$, $C(O) NR^2R^{2a}$, $C(O)NR^2(CH_2)_rOR^2$, $SO_2NR^2R^{2a}$, —$NR^2SO_2R^{2b}$, $C_{3-6}$ carbocyclic residue substituted with 0–2 $R^{4b}$, and 5–10 membered heterocyclic system containing from 1–4 heteroatoms selected from the group consisting of N, O, and S substituted with 0–2 $R^{4b}$;
$R^{1''}$, at each occurrence, is selected from H, CH(CH$_2$OR$^2$)2, $C(O)R^{2c}$, $C(O)NR^2R^{2a}$, $S(O)R^{2b}$, $S(O)_2R^{2b}$, and $SO_2NR^2R^{2a}$; $R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;
$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;
alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;
$R^{2b}$ is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;
$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^3$, at each occurrence, is selected from H, $C_{1-4}$ alkyl, and phenyl;

$R^{3a}$, at each occurrence, is selected from H, $C_{1-4}$ alkyl, and phenyl;

A is selected from:
  $C_{3-10}$ carbocyclic residue substituted with 0–2 $R^4$, and
  5–10 membered heterocyclic system containing from 1–4 heteroatoms selected from the group consisting of N, O, and S and substituted with 0–2 $R^4$;

B is selected from: H, Y, and X—Y;

X is selected from $C_{1-4}$ alkylene, —$CR^2(CR^2R^{2b})(CH_2)_t$—, —C(O)—, —C(=NR$^{1''}$)—, —$CR^2(NR^{1''}R^2)$—, —$CR^2(OR^2)$—, —$CR^2(SR^2)$—, —$C(O)CR^2R^{2a}$—, —$CR^2R^{2a}C(O)$, —$S(O)_p$—, —$S(O)_pCR^2R^{2a}$—, —$CR^2R^{2a}S(O)_p$—, —$S(O)2NR^2$—, —$NR^2S(O)2$—, —$NR^2S(C)_2CR^2R^{2a}$—, —$CR^2R^{2a}S(O)_2NR^2$—, —$NR^2S(O)2NR^2$—, —C(O)NR$^2$—, —NR$^2$C(O)—, —C(O)NR$^2$CR$^2$R$^{2a}$—, —NR$^2$C(O)CR$^2$R$^{2a}$—, $CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
  $(CH_2)_rNR^2R^{2a}$, provided that X—Y do not form a N—N, O—N, or S—N bond,
  $C_{3-10}$ carbocyclic residue substituted with 0–2 $R^{4a}$, and
  5–10 membered heterocyclic system containing from 1–4 heteroatoms selected from the group consisting of N, O, and S substituted with 0–2 $R^{4a}$;

$R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^2C$, $NR^2C(O)R^{2b}$, $C(O)NR^2R^{2a}$, $NR^2C(O)NR^2R^{2a}$, CH(=$NR^2$)$NR^2R^{2a}$, CH(=NS(O)$_2R^5$)$NR^2R^{2a}$, NHC(=$NR^2$)$NR^2R^{2a}$, C(O)NHC(=$NR^2$)$NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_rR^{1'}$, $O(CH_2)_2(CH_2)_rR^{1'}$, and $S(CH_2)_2(CH_2)_rR^{1'}$;

alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_rOR^2$, $(CH_2)_r$—F, $(CH_2)_r$—Br, $(CH_2)_r$—Cl, I, $C_{1-4}$ alkyl, —CN, $NO_2$, $(CH_2)_rNR^2R^{2a}$, $(CH_2)_rNR^2R^{2b}$, $(CH_2)_rC(O)R^2C$, $NR^2C(O)R^{2b}$, $C(O)NR^2R^{2a}$, $C(O)NH(CH_2)_2NR^2R^{2a}$, $NR^2C(O)NR^2R^{2a}$, CH(=$NR^2$)$NR^2R^{2a}$, NHC(=$NR^2$)$NR^2R^{2a}$, $SO_2NR^2R^{2a}$, $NR^2SO_2NR^2R^{2a}$, $NR^2SO_2$—$C_{1-4}$ alkyl, $C(O)NHSO_2$—$C_{1-4}$ alkyl, $NR^2SO_2R^5$, $S(O)_pR^5$, and $(CF_2)_rCF_3$;

alternatively, one $R^{4a}$ is a 5–6 membered aromatic heterocycle containing from 1–4 heteroatoms selected from the group consisting of N, O, and S;

$R^{4b}$, at each occurrence, is selected from H, =O, $(CH_2)_rOR^3$, F, Cl, Br, I, $C_{1-4}$ alkyl, —CN, $NO_2$, $(CH_2)_rNR^3R^{3a}$, $(CH_2)_rC(O)R^3$, $(CH_2)_rC(O)OR^3C$, $NR^3C(O)R^{3a}$, C(O)$NR^3R^{3a}$, $NR^3C(O)NR^3R^{3a}$, CH(=$NR^3$)$NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_rOR^2$, F, Cl, Br, I, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, CH(=NH)$NH_2$, NHC(=NH)$NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)_n$-phenyl;

$R^9$, at each occurrence, is selected from H, $C_{1-6}$ alkyl and $(CH_2)_n$-phenyl;

a, at each occurrence, is selected from 0, 1, and 2;
d, at each occurrence, is selected from 0 and 1;
n, at each occurrence, is selected from 0, 1, 2, and 3;
m, at each occurrence, is selected from 0, 1, and 2;
p, at each occurrence, is selected from 0, 1, and 2;
q, at each occurrence, is selected from 1 and 2;
r, at each occurrence, is selected from 0, 1, and 2;
s, at each occurrence, is selected from 0, 1, and 2; and,
t, at each occurrence, is selected from 0 and 1;
provided that A—B is other than benzyl-thiazolidin-2,4-dione.

[2] In a preferred embodiment, the present invention provides a novel compound of formula I, wherein;
one of W, $W^1$, $W^2$, and $W^3$ is C—D and the remaining are C—$R^1$;
J is selected from N(Z—A—B) and CR(Z—A—B); and
$J^a$ and $J^b$ together are selected from CONHCR$^e$R$^f$, $SO_2NHCR^eR^f$, $(CR^aR^b)_aSO_2NR^d$, and $(CR^aR^b)_bCOCO(CR^eR^f)_c$, wherein b+c=0 or 1;
alternatively, J and $J^a$ together are selected from CON(Z—A—B)(CR$^c$R$^b$) and N(Z—A—B)Q(R$^c$R$^b$)$_a$; and
$J^b$ is selected from $NR^d$, O, and CR$^e$R$^f$;
Q is CO;
alternatively, J, $J^a$ and $J^b$ together are selected from CR(Z—A—B)(CR$^a$R$^b$)$_a$QNR$^d$, CR(Z—A—B)(CR$^a$R$^b$)$_d$C(O)O, CR(Z—A—B) NHCOCR$^e$R$^f$, CR(Z—A—B) NHSO$_2$CR$^e$R$^f$, N(Z—A—B)(CR$^a$R$^b$)$_a$QNR$^d$, N(Z—A—B)(CR$^a$R$^b$)C(O)O, N(Z—A—B)SO$_2$(CR$^c$R$^b$)$_a$CR$^e$R$^f$, N(Z—A—B)SO$_2$(CR$^c$R$^b$)$_a$NR$^d$, CON(Z—A—B)CR$^e$R$^f$, and CONR$^b$(CR$^c$R$^b$)$_a$N(Z—A—B)

Z is selected from a $CH_2O$, $OCH_2$, $CH_2NH$, $NHCH_2$, $CH_2C(O)$, $C(O)CH_2$, $C(O)NH$, $C(O)NH$, $CH_2S(O)_2$, $S(O)_2$ $(CH_2)$, $SO_2NH$, and $SO_2NH$;
B is selected from: Y, X—Y, and $NR^2R^{2a}$;
Y is selected from one of the following carbocyclic and heterocyclic systems which are substituted with 0–2 $R^{4a}$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;
Y may also be selected from the following bicyclic heteroaryl ring systems:

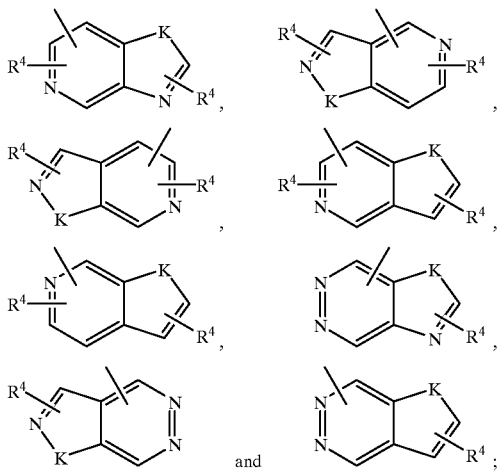

K is selected from O, S, NH, and N; and,
a, at each occurrence, is selected from 0 and 1.

[3] In an even more preferred embodiment, the present invention provides a novel compound of formula Ia,

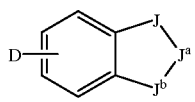

or stereoisomer or pharmaceutically acceptable salt thereof, wherein;

D is C(=NR$^7$) NR$^8$R$^9$;

J is selected from N(Z—A—B) and CR(Z—A—B); and

J$^a$ and J$^b$ together are selected from CONHCR$^e$R$^f$;

alternatively, J and J$^a$ together are selected from CON(Z—A—B)(CR$^e$R$^b$) and N(Z—A—B)Q(R$^c$R$^b$)$_a$; and J$^b$ is selected from NR$^d$, O, and CR$^e$R$^f$;

Q is CO;

alternatively, J, J$^a$ and J$^b$ together are selected from CR(Z—A—B)(CR$^a$R$^b$)$_a$QNR$^d$, CR(Z—A—B)(CR$^a$R$^b$)$_a$C(O)O, N(Z—A—B)(CR$^a$R$^b$)$_a$QNR$^d$, N(Z—A—B)(CR$^a$R$^b$)C(O)O, CON(Z—A—B)CR$^e$R$^f$, and CONR$^b$(CR$^e$R$^b$)$_a$N(Z—A—B);

A is selected from:
  piperidinyl,
  piperazinyl, C$_{5-6}$ carbocyclic residue substituted with 0–2 R$^4$, and
  5–6 membered heteroaryl containing from 1–4 heteroatoms
selected from the group consisting of N, O, and S and substituted with 0–2 R$^4$; and, B is selected from: Y and X—Y.

[4] In an even more preferred embodiment, the present invention provides a novel compound of formula Ia, wherein J and J$^a$ together are N(Z—A—B)C(O); and J$^b$ is selected from NR$^d$, O, and CR$^e$R$^f$;

alternatively, J, J$^a$ and J$^b$ together are CR(Z—A—B)C(O)NR$^d$;

Y is selected from one of the following carbocyclic and heterocyclic systems which are substituted with 0–2 R$^4$a;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazole, oxadiazole, thiadiazole, triazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,2,3-triazole, 1,2,4-triazole, 1,2,5-triazole, and 1,3,4-triazole.

[5] In a still further preferred embodiment, the present invention provides a novel compound selected from:
1N-(2'-Aminosulfonyl-[1,1']biphenylamino) carbonylmethyl-6- amidinobenzimidazolinone;
1N-(2'-Aminosulfonyl-[1,1']biphenylamino)-carbonylmethyl-5- amidinobenzimidazolinone;
1N-[4'-(p-chlorophenyl)thiazolyl-2'-amino)carbonylmethyl-6- amidinobenzimidazolinone;
5-Amidino-1N-(1'N-(4'- benzylpiperidino)carbonylmethyl) benzimidazolinone;
1N-(2'-Aminosulfonyl-[1,1']biphenylamino) carbonylmethyl-3N-0- hydroxyethylene-6- amidinobenzimidazolinone;
1N-(1'N-(2'-aminosulfonyl-[1,1']- biphenylamino) carbonylmethyl)-6-amidinobenzoxazolinone;
1N-(N-p-(41-oxazolyl)phenylamino)carbonylmethyl-6- amidino- benzoxazolinone;
1N-(1'N-(4'N-benzylsulfonylpiperazino)carbonylmethyl-6- amidino-benzoxazolinone;
7-amidino-1N-(4'-bromophenyl)carbonylmethyl-3,4-dihydroquinoxalin-2(1H)-one;
7-amidino-1N-(3'-amino-[1,1']biphenyl)carbonyl-methyl-3,4- dihydroquinoxalin-2(1H)-one;
7-amidino-1N-(43-fluoro-[1,1']biphenyl)carbonyl-methyl-3,4- dihydroquinoxalin-2(1H)-one;
7-amidino-1N-[1,1']-biphenylcarbonylmethyl-3,4-dihydroquinoxalin-2(1H)-one;
7-amidino-1N-(2'-tert-butylsulfonamido- [1,1']biphenyl) carbonylmethyl-3,4-dihydroquinoxalin- 2(1H)-one;
7-amidino-1N-(2'-sulfonamido-[1,1']-biphenyl)-carbonylmethyl- 3,4-dihydroquinoxalin-2(1H)-one;
1N-(2'-aminosulfonyl-[1,1']biphenylamino)carbonyl-methyl-7- amidino-3,4-dihydroquinoxalin-2(1H)-one;
6-amidino-1N-[1,1']-biphenyl)carbonylmethyl-3,4-dihydroquinoxalin-2(1H)-one;
1N-[1,1']Biphenylcarbonyl)ethyl-6-amidinobenzoxazolinone;
1-([1,1']-Biphenylcarbonyl)ethyl-6-amidino-3N- methyl-benzimidazolinone;
1-([1,1']-biphenylcarbonyl)ethyl-6-amidinobenzimidazolinone;
1N-(4-Bromophenylcarbonyl)ethyl-6-amidinobenzoxazolinone; 1N-[4-(2-Aminosulfonylphenyl)pyridin-2-yl] aminocarbonylmethyl- 6-amidinobenzoxazolinone;
1N-(4-Morpholinosulfonamidophenyl) aminocarbonylmethyl-6- amidinobenzoxazolinone;
3-(3-methoxy-(2'-aminosulfonyl-[1,1']biphenyl-1-aminocarbonyl)methyl-5-amidino-2-indolinone;
3-(3-amino-(2'-aminosulfonyl-[1,1']--biphenylaminocarbonyl)methyl-5-amidino-2-indolinone;
3-(3-hydroxy-(2'-aminosulfonyl-[1,1']-biphenylaminocarbonyl)methyl-5-amidino-2-indolinone;
3-(3'-hydroxy-(2-chloro-(21-aminosulfonyl)-[1,1']-biphenylaminocarbonyl)methyl-5-amidino-2-indolinone;
3-(3'-amino-(2-chloro-(2'-aminosulfonyl)-[1,1']-biphenylaminocarbonyl)methyl-5-amidino-2-indolinone;
3-(2-chloro-(2'-aminosulfonyl)-[1,1']biphenyl-31-aminocarbonyl)methyl-5-amidino-2-indolinone;
3-(2-bromo-(2'-aminosulfonyl)-[1,1']biphenyl-31-aminocarbonyl)methyl-5-amidino-2-indolinone;

3-(2-fluoro-(2'-aminosulfonyl)-[1,1']biphenyl-3'-aminocarbonyl)methyl-5-amidino-2-indolinone; and,
3-(2'-aminosulfonyl)-[1,1']biphenyl-3'-aminocarbonyl)methyl-5- amidino-2-indolinone.

[6] In another preferred embodiment, the present invention provides a compound of the formulae a–c:

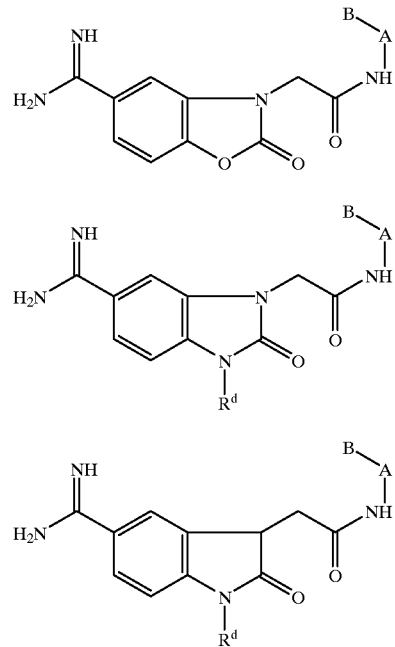

or stereoisomer or pharmaceutically acceptable salt form thereof.

In a preferred embodiment, the present invention provides a compound of the formula:

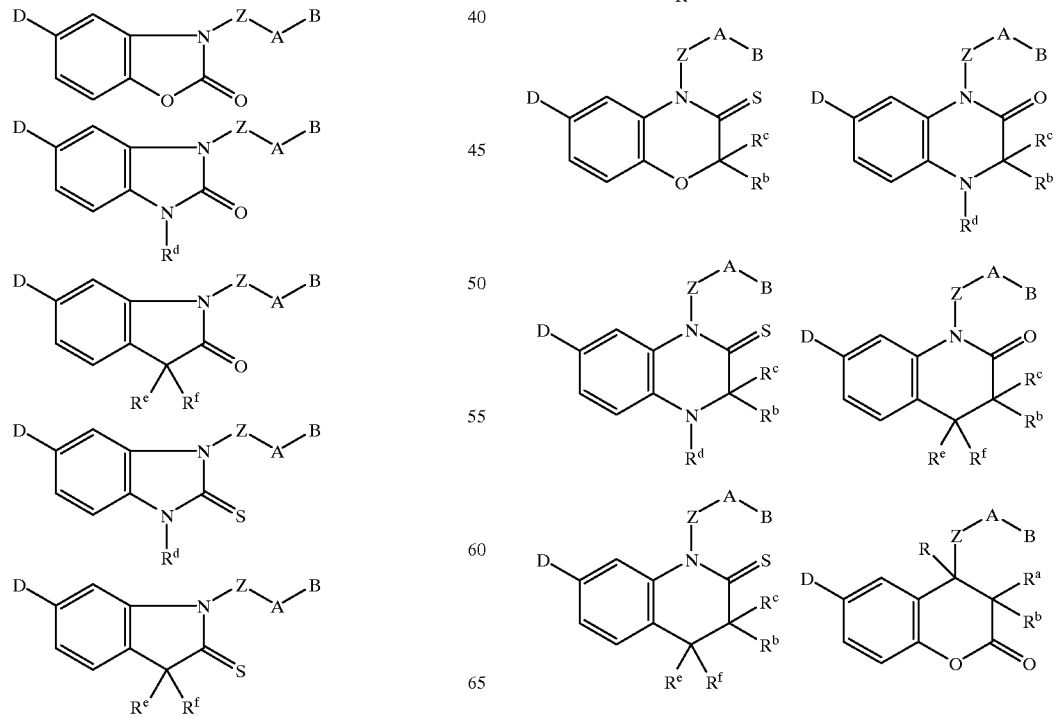

-continued
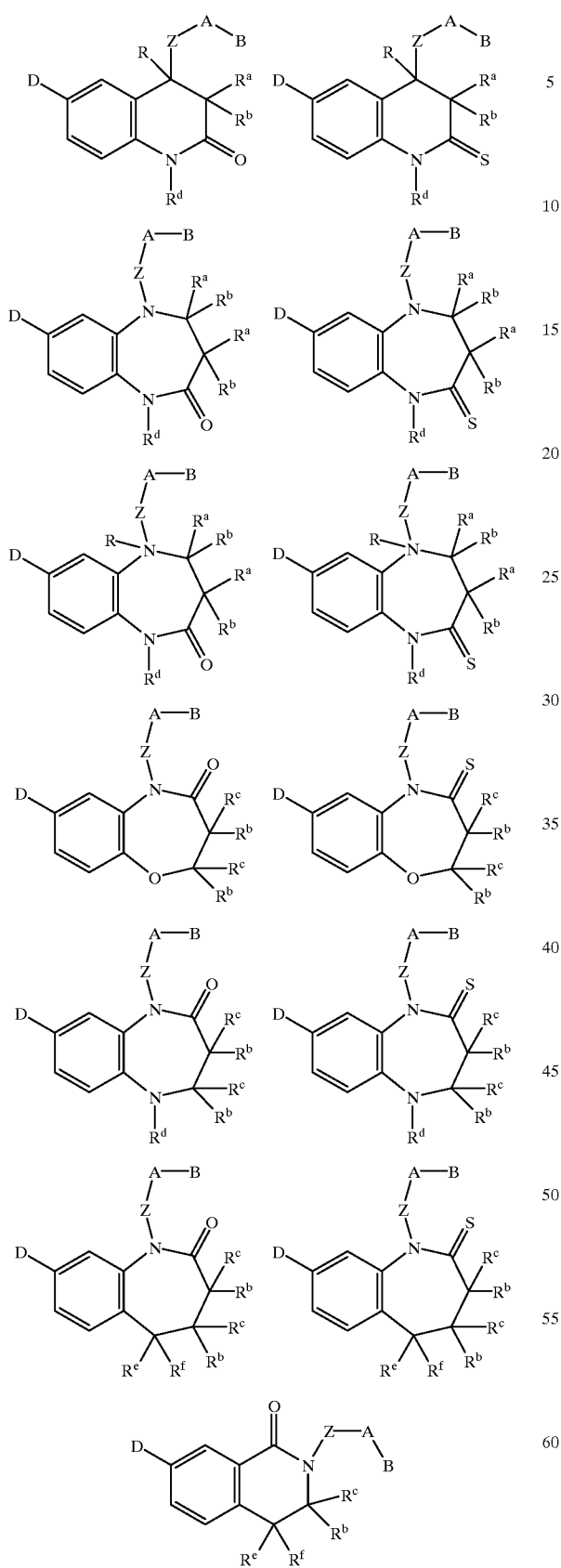
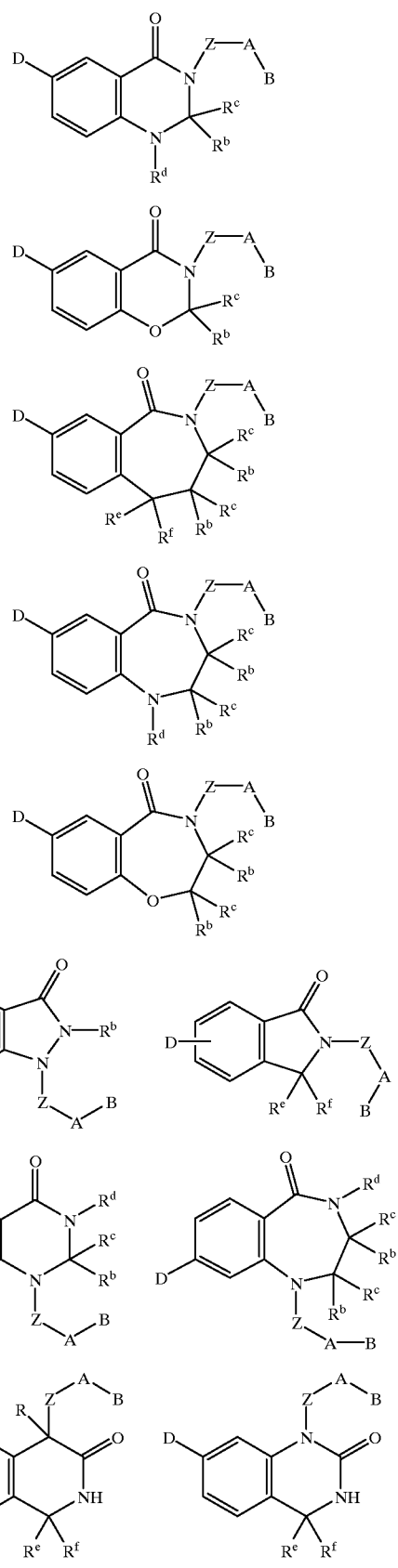

-continued

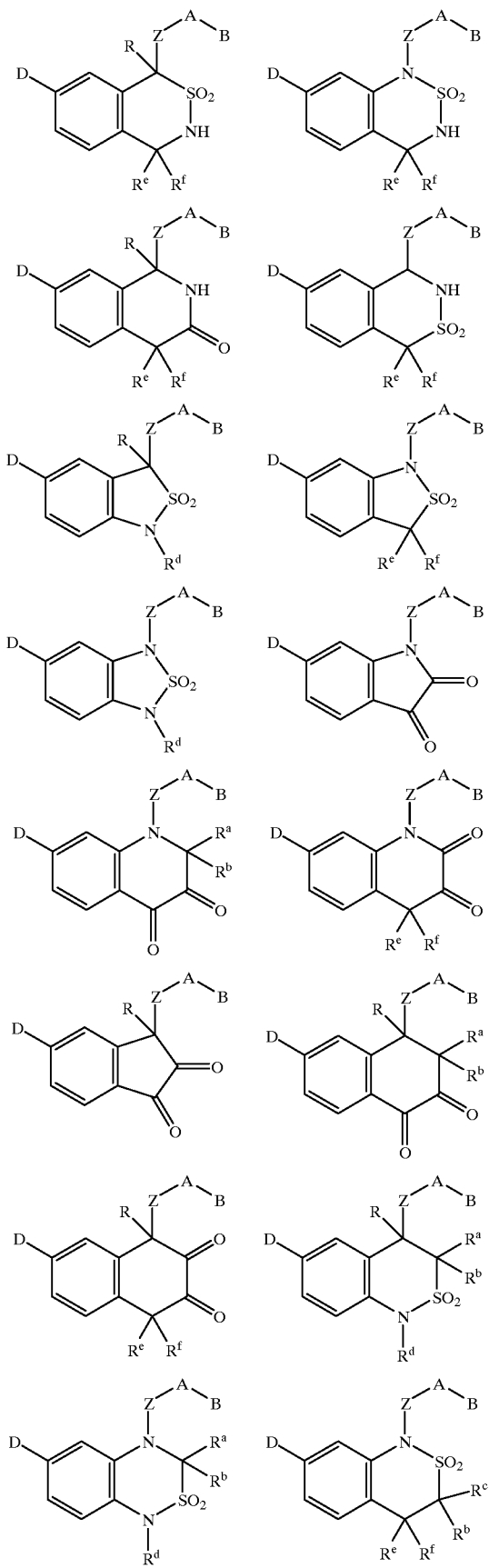
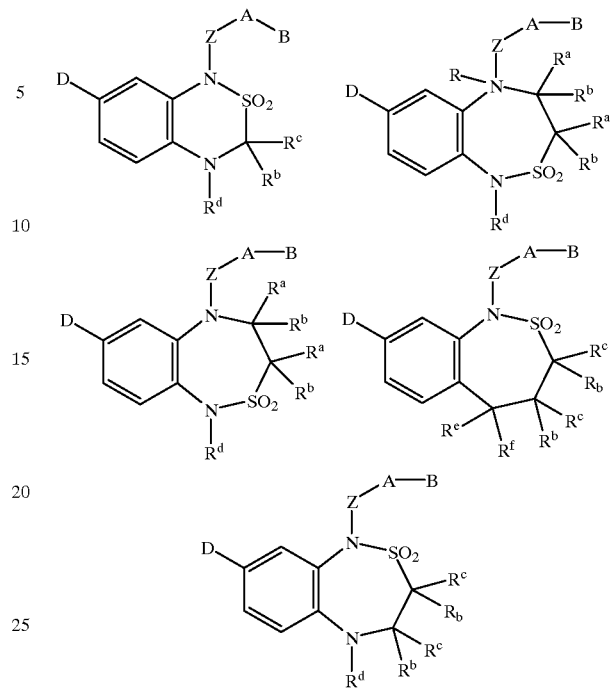

In a third embodiment, the present invention provides novel pharmaceutical compositions, comprising: a pharmaceutically acceptable carrier and a therapeutically effective amount of a compound of formula (I) or a pharmaceutically acceptable salt form thereof.

In a fourth embodiment, the present invention provides a novel method for treating or preventing a thromboembolic disorder, comprising: administering to a patient in need thereof a therapeutically effective amount of a compound of formula (I) or a pharmaceutically acceptable salt form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon-carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7- membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" is intended to mean a stable 5- to 7- membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H- 1,5,2-dithiazinyl, dihydrofuro [2,3-b]tetrahydrofuran, furanyl, furazanyl, imidazolidinyl, imidazolinyl, imidazolyl, 1H- indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoguinolinyl, oxadiazolyl, 1,2,3-oxadiazolyl, 1,2,4- oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5- thiadiazinyl, 1,2,3-thiadiazolyl, 1,2,4-thiadiazolyl, 1,2,5- thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amine prodrugs the amine group is attached to a group selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of Formula I can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis,* Wiley and Sons, 1991).

Scheme 1

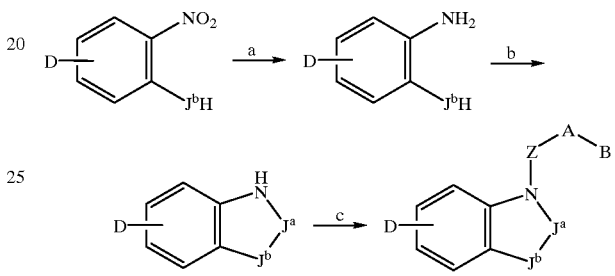

The generic cores depicted in Scheme 1 can be made from nitro compounds or from the replacement of the corresponding halogen with the $HNR^d$- or HO-fragments in the presence of a base. Reduction of the nitro group can provide anilines. Cyclization of the anilines with formic acid, trialkylorthoformate, phosgene, carbon disulfide, sulfuryl chloride, oxalyl chloride, α-chloroacetyl chloride, β-chloroacetyl chloride, α-chloroacetal, β-chloroacetate, α-chlorosulfonyl chloride, or β-chlorosulfonyl chloride can form the cyclic cores. Alkylation of the NH on the new formed ring with halo-ZAB can provide the desired compound.

The thioamides and thioesters of the present invention can be obtained from the corresponding amides and esters by treatment with $P_2S_5$ in the presence of a base, or with Lawesson's reagent (T. Nishio et al, *Synthesis* 1989, 5, 396).

Scheme 2

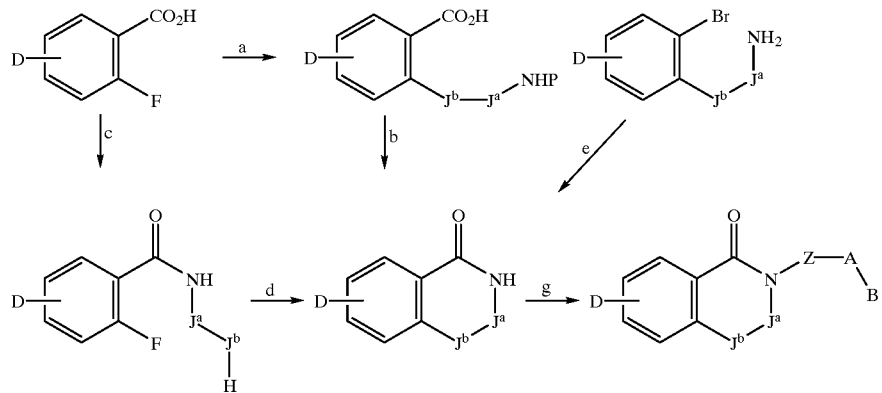

The 6,6-fused compounds described in Scheme 2 can be prepared starting with nucleophilic substitution of the aryl fluoride with HJ$^a$J$^b$NHP in the presence of a base. fter removal of the protecting group P, intramolecular cyclization with a dehydration reagent can give the desired cores. Alternatively, dehydration of the acid with HJ$^a$J$^b$NH$_2$, followed by intramolecular nucleophilic substitution of the aryl fluoride by the J$^b$H-fragment in the presence of a base, can give the desired cores. Furthermore, Ω-(2-bromo- phenyl)alkylamines can react with carbon monoxide in the presence of palladium catalyst to give the desired cores.

Scheme 3

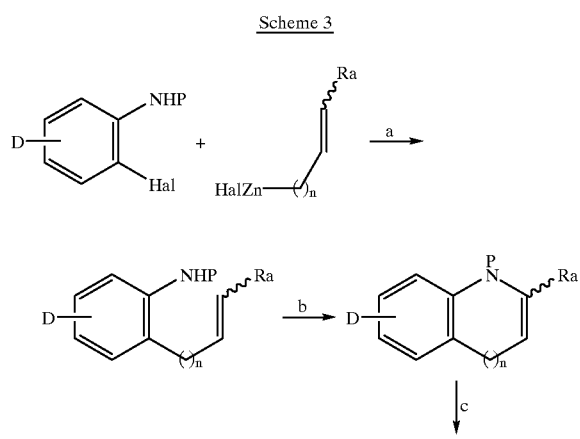

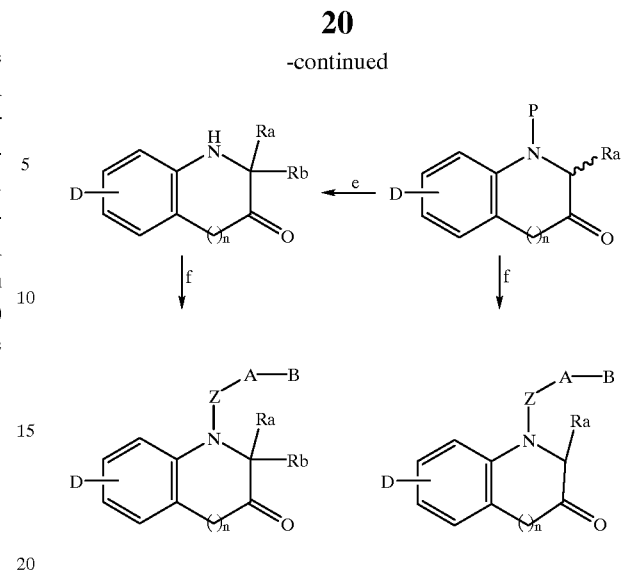

The generic cores depicted in Scheme 3 can be prepared from N-protected o-halo-anilines. The anilines can also be made from the non-protected anilines or the nitro precursors. Palladium catalyzed coupling reaction of the halides with zinc reagents containing vinyl functionality can give the coupled compounds. In the presence of palladium catalyst. intramolecular cyclizations can produce ring closed compounds, which can be oxidized with MCPBA to give the 3-oxo cores. The 3-oxo derivatives can be further elaborated, followed by the N-alkylation with halo-ZAB, to provide the desired compounds.

Scheme 4

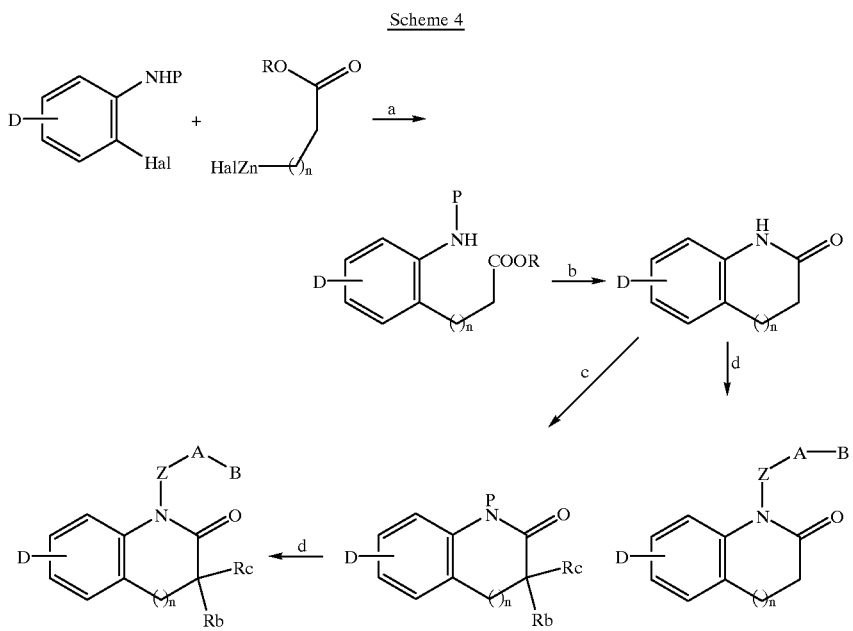

The N-substituted cores illustrated in Scheme 4 can be obtained from N-protected o-halogen anilines. Metal catalyzed coupling of the halide with a zinc reagent which contains an ester functionality can give the coupled compound. Deprotection of the P-group from the nitrogen can give the cyclic compound. Further elaboration and N-alkylation can be performed as described previously.

Scheme 5

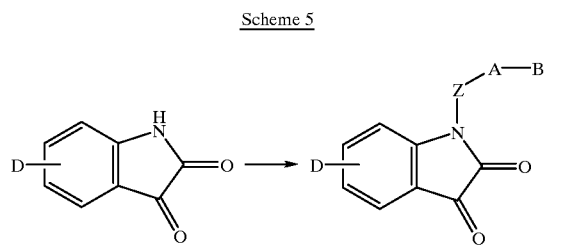

Bromine on commercially available 5-bromoisatin can be converted to other functionalities by palladium catalyzed cross coupling reactions and nucleophilic replacements. The desired compounds can then be obtained by N-alkylation with halo-ZAB.

Scheme 6

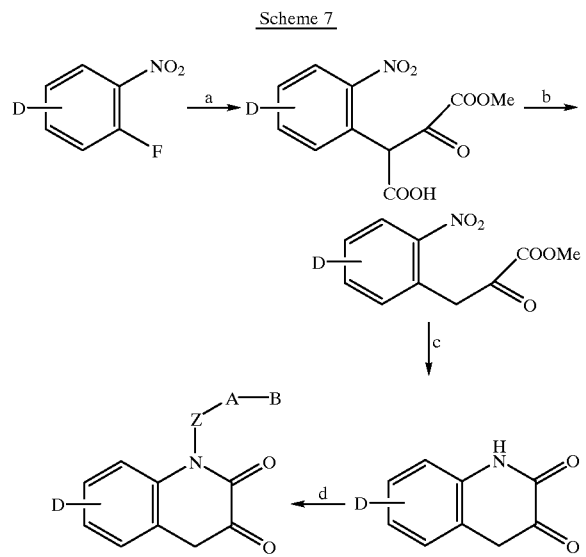

Scheme 6 provides a route to some of the diketones of the present invention. Oxidation of o-allylaniline (see Scheme 3) with $MnO_2$ can provide a ketone. The ketone can then undergo Michael addition, followed by quenching with chlorosilane, to give the cyclic vinyl silylether. The vinyl silylether can be oxidized with NMMO in the presence of $OsO_4$ to form the α-hydroxyketone, which can be further oxidized with $Pb(OAc)_4$ in pyridine to form the diketone.

The desired compound can be obtained by N-alkylation with an appropriate halo-ZAB.

Scheme 7

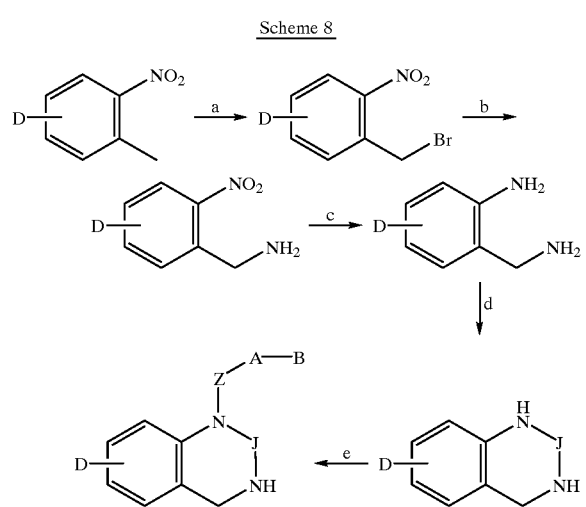

Preparation of additional diketones is shown in Scheme 7. Nucleophilic substitution of the aryl fluoride with 2-ketosuccinic acid monomethyl ester, followed by decarboxylation, can give β-aryl-α-ketoester. Protection of the carbonyl group, reduction of the nitro group, and deprotection of the carbonyl group can afford the final intermediate which is then cyclized and alkylated.

Scheme 8

6,6-Fused ureas/sulfonylureas can be made as shown in Scheme 8 (J=CO, $SO_2$). Bromination of 2-methyl nitrobenzene with NBS can give the benzyl bromide, which can be readily converted into the amine. After reduction of the nitro group, cyclization with $COCl_2$ or $SO_2Cl_2$ can afford the desired cores.

Scheme 9

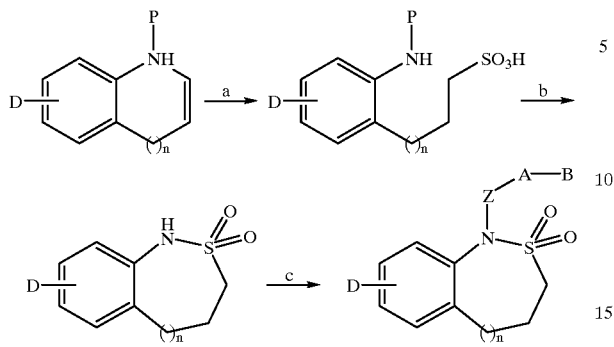

Scheme 9 illustrates a route to fused sulfonamides. Addition of NaHSO$_3$ to the olefin (see Scheme 3) can give the corresponding sulfuric acid (Li, C. *Synthesis* 1991, 244). Removal of the P-group and then dehydration with the sulfuric acid can provide sulfonamide, which can undergo N-alkylation to afford the desired products.

Scheme 10

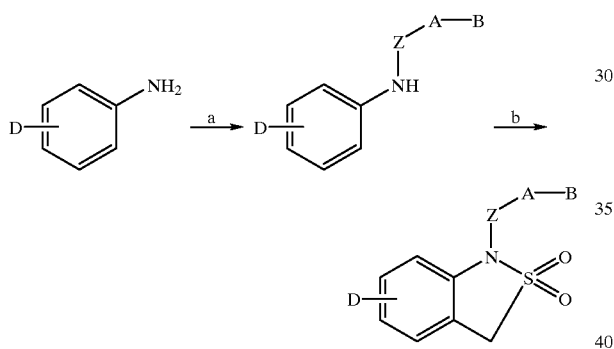

In Scheme 10 is shown a route to a 6,5-fused sulfonamide. N-alkylation of the aniline with halo-ZAB, followed by treatment with ClCH$_2$SO$_2$Cl and a base, can give the desired core (Wojciechowski, K. *Synthesis* 1992, 571).

Scheme 11

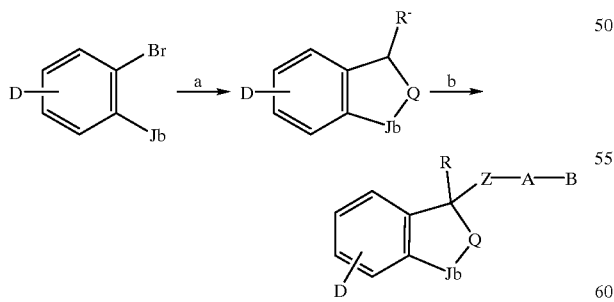

The 6,5-fused heterocyclic rings wherein J$^b$ is N-R$^d$ or O are prepared by rhodium coupling with an appropriate azide, Cl—Q—CH(R)N$_2$ (Scheme 11). Deprotonation of the benzylic -methine with LDA at followed by addition of the corresponding halo-ZAB affords the desired product.

Scheme 12

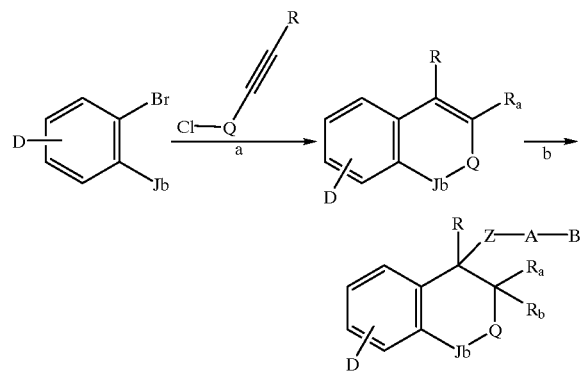

Synthesis of the 6,6-fused heterocycles (J$^b$ is N-R$^d$ or O) may be obtained via radical addition to an acetylene derivative as shown (e.g., Bu$_3$SnH) or transmetallation of the aromatic bromine with n-BuLi or palladium coupling with Pd(OAc)$_2$ and finally quenching with the desired Ra-halo compound to afford the intermediate shown in Scheme 12. Cuprate addition (Li(CN)Cu—Z—A—B) and quenching again with the appropriate R$^b$-halo compound should afford the desired 6,6- fused heterocycle target.

Scheme 13

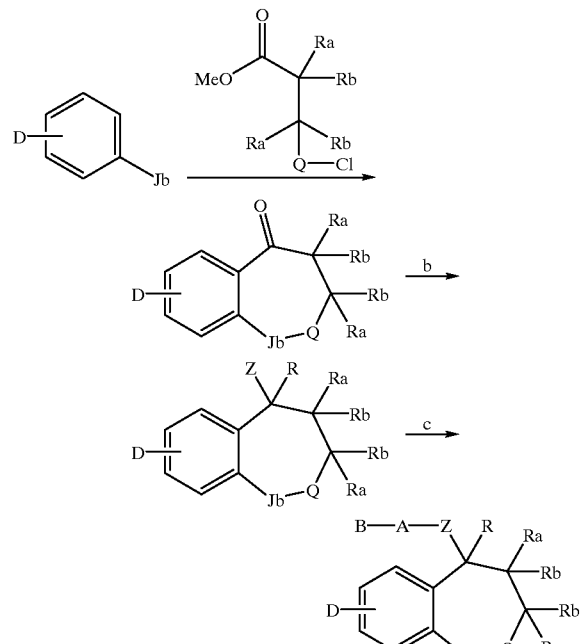

Acylation of an anilino or phenolic starting reagent (J$^b$=N—R$^d$ or O) with a functionalized methyl ester acid chloride followed by saponification should afford the desired acid intermediate (Scheme 13). Chlorination to the acid chloride with thionyl chloride can afford the acid chloride intermediate which can then subjected to the Friedel Crafts conditions to afford the target heterocycle. The resulting heterocycle may be further functionalized via a Wittig olifination, followed by hydrogenation and alkylation to yield the fully functionalized heterocycle. The benzylic Z-group can then coupled to the A—B groups to afford the target compound.

Scheme 14

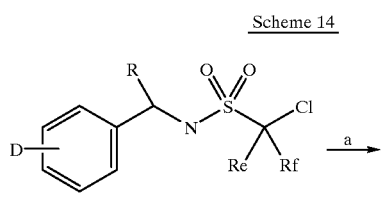

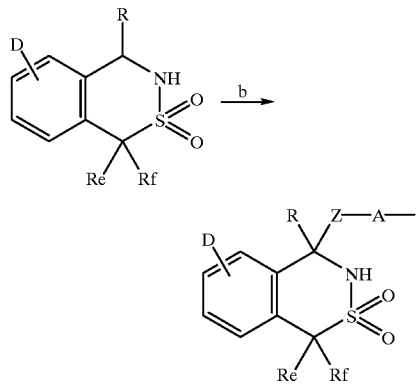

The 6,6 sulfonamides in Scheme 14 may be prepared from the appropriate halo sulfonamide using NaOH and DMSO (*Synthesis* 1992, (6), 571–6). Alkylation with NaH and halo-ZAB should afford the desired target. This same method may be used to prepared the 6,6-fused cyclic amides in Scheme 15.

Scheme 15

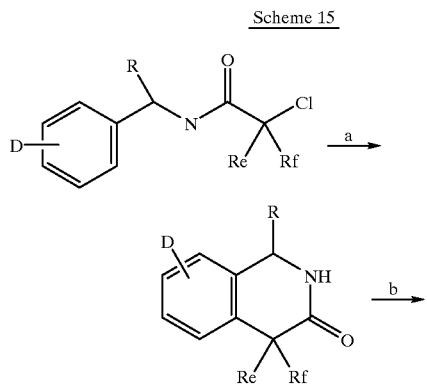

Scheme 16

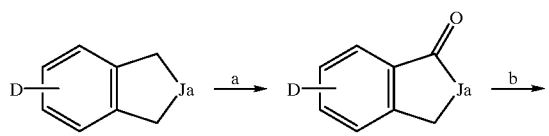

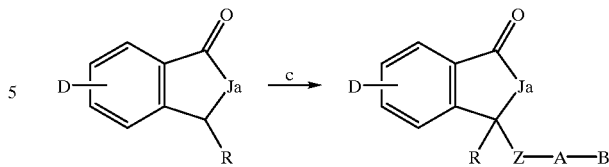

5,6-Fused isatins can be prepared from the corresponding indanone (Scheme 16). Oxidation with $SeO_2$ in acetic acid followed by alkylation or bromination/hydrolysis should afford the key isotin intermediate (*J. Chem. Soc., Perkin Trans.* 1995, 1(24), 3117–24). This may then alkylated with the corresponding halo-ZAB to afford the desired isatin target.

Scheme 17

The 6,6-fused carbocycles shown in Scheme 17 may be prepared from the corresponding 3-tetralone via alkylation with NaH R-halo or NBS, followed by a second alkylation with halo-ZAB. Oxidation with $SeO_2$ affords the desired diketone which is then dialkylated with $R^e$-halo and $R^f$-halo sequentially using NaH as the base to yield the desired target.

Preparation of group A—B of FORMULA I

Compounds of this invention where B is either a carbocyclic or heterocyclic residue as defined in Formula I are coupled to A as shown generically and by specific example in Schemes 18 and 19, respectively. Either or both of A and B may be substituted with 0–2 $R^4$. W is defined as a suitable protected nitrogen, such as $NO_2$ or NHBOC; a protected sulfur, such as S—tBu or SMOM; or a methyl ester. Halogen-metal exchange of the bromine in bromo-B with n-butyl lithium, quenching with triisopropyl borate and acidic hydrolysis gives the required boronic acid, B—B $(OH)_2X$ The W—A—Br subunit may be already linked to ring M before the Suzuki coupling reaction. Deprotection provides the complete subunit.

Scheme 18

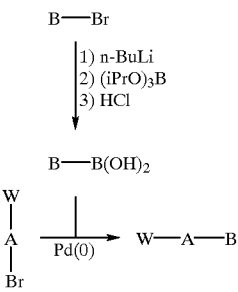

Scheme 19 describes a typical example of how the A—B subunit is prepared for attachment to ring M. 4-Bromoaniline is protected as Boc-derivative and the coupled to 2-(t- butylamino)sulfonylphenylboronic acid under Suzuki conditions. 30 2-(t-Butylamino) sulfonylphenylboronic acid is prepared by the method described by Rivero (*Bioorg. Med. Chem. Lett.* 1994, 189). Deprotection with TFA can provide the aminobiphenyl compound. The aminobiphenyl is then coupled to the core ring structures as described below.

Scheme 19

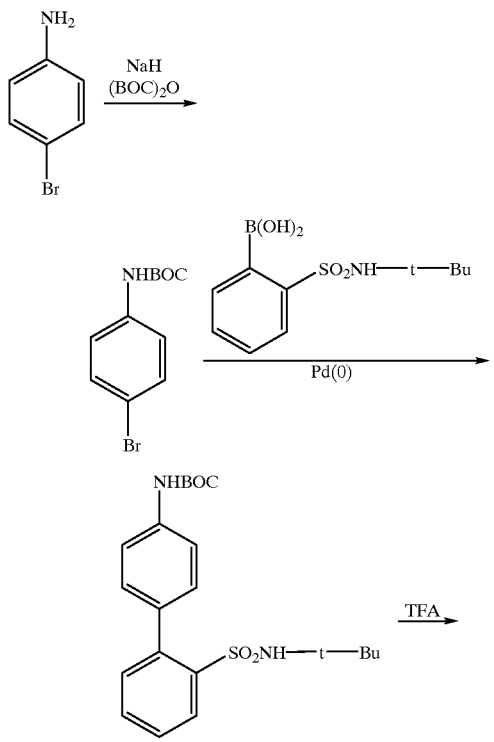

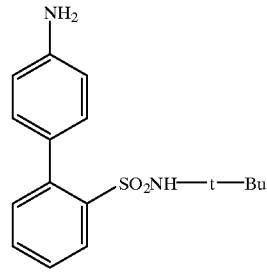

When B is defined as X—Y, the following description applies. Groups A and B are available either through commercial sources, known in the literature or readily synthesized by the adaptation of standard procedures known to practitioners skilled in the art of organic synthesis. the required reactive functional groups appended to analogs of A and B are also available either through commercial sources, known in the literature or readily synthesized by the adaptation of standard procedures known to practitioners skilled in the art of synthesis. In the tables that follow the chemistry required to effect the coupling of A to B is outlined.

TABLE A

Preparation of Amide Ester, Urea, Sulfonamide and Sulfamide Linkages Between A and B.

| If A contains | then the reactive substituent of Y is: | to give the following product A—X—Y: |
|---|---|---|
| A—NHR$^2$ as a substituent | ClC(O)—Y | A—NR$^2$—C(O)—Y |
| a secondary NH NH as part of a ring or chain | ClC(O)—Y | A—C(O)—Y |
| A—OH as a substituent | ClC(O)—Y | A—O—C(O)—Y |
| A—NHR$^2$ as a substituent | ClC(O)—CR$^2$R$^{2a}$—Y | A—NR$^2$—C(O)—CR$^2$R$^{2a}$—Y |
| a secondary NH as part of a ring or chain | ClC(O)—CR$^2$R$^{2a}$—Y | A—C(O)—CR$^2$R$^{2a}$—Y |
| A—OH as a substituent | ClC(O)—CR$^2$R$^{2a}$—Y | A—O—C(O)—CR$^2$R$^{2a}$—Y |
| A—NHR$^2$ as a substituent | ClC(O)—CNR$^2$—Y | A—NR$^2$—C(O)—CNR$^2$—Y |
| a secondary NH as part of a ring or chain | ClC(O)—CNR$^2$—Y | A—C(O)—CNR$^2$—Y |
| A—OH as a substituent | ClC(O)—CNR$^2$—Y | A—O—C(O)—CNR$^2$—Y |
| A—NHR$^2$ as a substituent | ClSO$_2$—Y | A—NR$^2$—SO$_2$—Y |
| a secondary NH as part of a ring or chain | ClSO$_2$—Y | A—SO$_2$—Y |
| A—NHR$^2$ as a substituent | ClSO$_2$—CR$^2$R$^{2a}$—Y | A—NR$^2$—SO$_2$—CR$^2$R$^{2a}$—Y |
| a secondary NH as part of a ring or chain | ClSO$_2$—CR$^2$R$^{2a}$—Y | A—SO$_2$—CR$^2$R$^{2a}$—Y |
| A—NHR$^2$ as a substituent | ClSO$_2$—NR$^2$—Y | A—NR$^2$—SO$_2$—NR$^2$—Y |
| a secondary NH as part of a ring or chain | ClSO$_2$—NR$^2$—Y | A—SO$_2$—NR$^2$—Y |
| A—C(O)Cl | HO—Y as a substituent | A—C(O)—O—Y |
| A—C(O)Cl | NHR$^2$—Y as a substituent | A—C(O)—NR$^2$—Y |
| A—C(O)Cl | a secondary NH as part of a ring or chain | A—C(O)—Y |

TABLE A-continued

Preparation of Amide Ester, Urea, Sulfonamide and Sulfamide Linkages Between A and B.

| If A contains | then the reactive substituent of Y is: | to give the following product A—X—Y: |
|---|---|---|
| A—CR$^2$R$^{2a}$-C(O)Cl | HO—Y as a substituent | A—CR$^2$R$^{2a}$C(O)—O—Y |
| A—CR$^2$R$^{2a}$-C(O)Cl | NHR$^2$—Y as a substituent | A—CR$^2$R$^{2a}$C(O)—NR$^2$—Y |
| A—CR$^2$R$^{2a}$-C(O)Cl | a secondary NH as part of a ring or chain | ALCR$^2$R$^{2a}$C(O)—Y |
| A—SO$_2$Cl | NHR$^2$—Y as a substituent | A—SO$_2$—NR$^2$—Y |
| A—SO$_2$Cl | a secondary NH as part of a ring or chain | A—SO$_2$—Y |
| A—CR$^2$R$^{2a}$-SO$_2$Cl | NHR$^2$—Y as a substituent | A—CR$^2$R$^{2a}$SO$_2$—NR$^2$—Y |
| A—CR$^2$R$^{2a}$-SO$_2$Cl | a secondary NH as part of a ring or chain | A—CR$^2$R$^{2a}$SO$_2$—Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of Ketone Linkages between A and B.

| If A contains: | then the reactive substituent of Y is: | to give the following product A—X—Y: |
|---|---|---|
| A—C(O)Cl | BrMg—Y | A—C(O)—Y |
| A—CR$^2$R$^{2a}$C(O)Cl | BrMg—Y | A—CR$^2$R$^{2a}$C(O)—Y |
| A—C(O)Cl | BrMbCR$^2$R$^{2a}$—Y | A—C(O)CR$^2$R$^{2a}$—Y |
| A—CR$^2$R$^{2a}$C(O)Cl | BrMgCR$^2$R$^{2a}$—Y | A—CR$^2$R$^{2a}$C(O)CR$^2$R$^{2a}$—Y |

The coupling chemistry of table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can reacted directly under very controlled conditions, that is low temperature (−20° C. or lower) and with a large excess of acid chloride or with catalytic or stoichiometric copper bromideedimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 601, 1955) or coupling mediated by Fe(acac)$_3$ according to Fiandanesse et al. (Tet. Lett., 4805, 1984), or a coupling mediated by manganese(II) catalysis (Cahiez and Laboue, Tet. Lett., 33(31), 4437, 1992).

TABLE C

Preparation of Ether and Thioether linkages between A and B.

| If A contains: | then the reactive substituent of Y is: | to give the following product A—X—Y: |
|---|---|---|
| A—OH | Br—Y | A—O—Y |
| A—CR$^2$R$^{2a}$—OH | Br—Y | A—CR$^2$R$^{2a}$O—Y |
| A—OH | Br—CR$^2$R$^{2a}$—Y | A—OCR$^2$R$^{2a}$—Y |
| A—SH | Br—Y | A—S—Y |
| A—CR$^2$R$^{2a}$—SH | Br—Y | A—CR$^2$R$^{2a}$S—Y |
| A—SH | Br—CR$^2$R$^{2a}$—Y | A—SCR$^2$R$^{2a}$—Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at a temperature ranging from ambient to the reflux point of the solvent used.

TABLE D

Preparation of —SO— and —SO$_2$—linkages from thioether of Table C.

| If the starting material is: | then it is oxidized with wet Alumina/Oxone to give: | then it is oxidized with m-chloroperbenzoic acid to give: |
|---|---|---|
| A—S—Y | A—S(O)—Y | A—SO$_2$—Y |
| A—CR$^2$R$^{2a}$S—Y | A—CR$^2$R$^{2a}$S(O)—Y | A—CR$^2$R$^{2a}$SO$_2$—Y |
| A—SCR$^2$R$^{2a}$—Y | A—S(O)CR$^2$R$^{2a}$—Y | A—SO$_2$CR$^2$R$^{2a}$—Y |

The thioethers of Table C serve as a convenient starting material for the preparation of the sulfoxide and sulfone analogs of Table D. A combination of wet alumina and Oxone can provide a reliable reagents for the oxidation of the thioether to the sulfoxide as shown by Greenhalgh (*Syn. Lett.* 1992, 235). The sulfone can be prepared according to the method of Satoh (*Chem. Lett.* 1992, 381) using m-chloroperbenzoic acid.

A compund of Formula I may have more than one isomer and one of the isomers may display superior activity compared with the other. Thus, each isomer is contemplated to be a part of the present invention. For example, both stereoisomers of the following indolinones are considered to be part of the present invention.

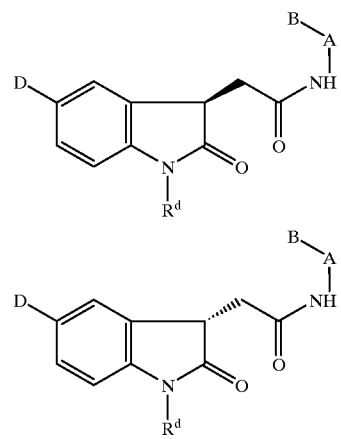

When required, separation of the racemic material can be achieved by HPLC using a chiral column or by a resolution using a resolving agent such as camphonic chloride as in Steven D. Young, et al, *Antimicrobial Agents and Chemotheraphy*, 1995, 2602–2605. A chiral compound of Formula I may also be directly synthesized using a chiral catalyst or a chiral ligand, e.g. Andrew S. Thompson, et al, *Tet. lett.* 1995, 36, 8937–8940. In addition, separation may be achieved by selective cystallization, optionally in the presence of a chiral acid or base thereby forming a chiral salt.

Other features of the invention will become apparent in the course of the following descriptions of exemplary embodiments which are given for illustration fo the invention and are not intended to be limiting thereof.

EXAMPLES

Examples 1 and 2

1N-(2'-Aminosulfonyl-[1,1']biphenylamino) carbonylmethyl-6- amidinobenzimidazolinone (Example 1) and 1-(2'-Aminosulfonyl- [1,1'] biphenylamino)-carbonylmethyl-5- amidinobenzimidazolinone (Example 2)

Preparation of 6—Cyanobenzimidazolinone.

After 4-amino-3-nitrobenzonitrile (3.26 g, 20 mmol) was treated with hydrogen in MeOH (300 mL) in the presence of 5% palladium on active carbon (1 g) at room temperature for 16 hours, the reaction mixture was filtered and the filtrate was concentrated to give 3,4-diaminobenzonitrile (2.4 g, 90% yield). A solution of 3,4-diaminobenzonitrile (2 g, 15 mmol) in THF (100 mL) was treated with carbonyldiimidazole (CDI, 3.2 g, 19 mmol) at room temperature for 18 hours. The mixture was diluted with EtOAc (150 mL), washed with 1N HCl (30 mL) and brine, and dried over $MgSO_4$. Filtration and concentration gave 5-cyanobenzimidazolinone (1.9 g, 80%). $^1H$ NMR $(CD_3OD)$ δ 7.40 (dd, J=8.1 Hz, J=1.5 Hz, 1H), 7.34 (d, J=1.5 Hz, 1H), 7.15 (d, J=8.1 Hz, 1H); MS: 160.1 $(M+H)^+$.

Preparation of 2'-tert-butylaminosulfonyl- [1,1'] biphenylaminocarbonylmethylene chloride.

Acylation of 4-[(o—$SO_2$NHtBu)-phenyl]aniline (3 mmol) with 2-chloroacetyl chloride (4 mmol) in $CH_3CN$ (100 mL) in the presence of $K_2CO_3$ (4 mmol) was carried out at rt for 16 hours. The mixture was filtered. The filtrate was extracted with EtOAc, washed with water, dried over $MgSO_4$, and concentrated to give the product in almost quantitative yield. $^1H$ NMR $(CD_3OD)$ δ 8.34 (s, 1H), 8.17 (d, J=8.1 Hz, 1H), 7.67 (d, J=8.4 Hz, 2H), 7.59–7.46 (m, 2H), 7.53 (d, J=8.8 Hz, 2H), 7.30 (dd, J=7.6 Hz, J=1.5 Hz, 1H), 4.23 (s, 2H), 3.58 (s, 1H), 1.02 (s, 9H); MS(CI). m/z 381 $(M+H)^+$.

Preparation of 1N-(2'-tert-butylaminosulfonyl- [1,1'] biphenylamino)carbonylmethyl-6-cyanobenzimidazolinone and 1N-(2'-tert-butylaminosulfonyl- [1,1']biphenylamino) carbonylmethyl-5-cyano-benzimidazolinone.

A solution of 5-cyanobenzimidazolinone (159 mg, 1 mmol) in DMF (5 mL) was treated with NaH (4 mmoL), followed by addition of 1N-(2'-tert-butylaminosulfonyl-[1, 1']- biphenylamino)carbonylmethyl chloride (380 mg, 1 mmol). The resulting mixture was stirred at room temperature for 18 hours, and then was extracted with EtOAc. The organic layer was washed with water and brine, and dried over $MgSO_4$, followed by purification and isolation on HPLC, to give 1N- (2'-tert-butylaminosulfonyl-[1,1l]-biphenylamino)- carbonylmethyl-6-cyanobenzimidazolinone (80 mg, 16%) and 1N- (2'-tert-butylaminosulfonyl-[1,1']-biphenylamino)-carbonylmethyl-5-cyanobenzimidazolinone (120 mg, 24%). Both regioisomers have ESMS m/z: 465 (M+H). For the 6-cyano isomer: $^1H$ NMR $(CD_3OD)$ δ 8.11 (dd, J=8.4 Hz, J=1.2 Hz, 1H), 7.63 (d, J=8.5 Hz, 2H), 7.63–7.62 (m, 1H), 7.51 (td, J=7.8 Hz, J=1.5 Hz, 1H), 7.47 (dd, J=8.4 Hz, J=1.5 Hz, 1H), 7.43 (d, J=8.5 Hz, 2H), 7.43–7.42 (m, 1H), 7.32 (dd, J=7.7 Hz, J=1.4 Hz, 1H), 7.26 (d, J=8.1 Hz, 1H), 4.82 (s, 2H), 0.99 (s, 9H); $^{13}C$ NMR $(CD_3OD)$ δ 167.28, 156.85, 143.46, 141.60, 139.10, 137.26, 135.85, 133.90, 133.05, 131.49, 130.16, 129.53, 128.75, 127.52, 120.59, 120.42, 113.58, 110.14, 105.64, 54.99, 44.56, 30.06. For the 5-cyano isomer: $^1H$ NMR $(CD_3OD)$ δ 8.08 (dd, J=8.1 Hz, J=1.2 Hz, 1H), 7.63–7.56 (m, 3H), 7.49 (td, J=7.8 Hz, J=1.5 Hz, 1H), 7.43–7.42 (m, 1H), 7.40 (d, J=7.2 Hz, 2H), 7.30 (dd, J=7.6 Hz, J=7.6 Hz, 1H), 7.24 (d, J=8.4 Hz, 1H), 7.20 (d, J=8.3 Hz, 1H), 2.01 (s, 2H), 0.99 (s, 9H).

Preparation of 1N-(2'-aminosulfonyl-[1,1')]-biphenylamino)carbonylmethyl-6-amidinobenzimidazolinone and 1N-(2'-aminosulfonyl-[1, 1']-biphenylamino)carbonylmethyl-5- amidinobenzimidazolinone.

A solution of 1N-(2'-tert-butylaminosulfonyl-[1,1']-biphenylamino)carbonylmethyl-6-cyanobenzimidazolinone (0,16 mmol) in EtOH (10 mL) was saturated with HCl gas and stirred at 0° C. for 16 hours. The solution was concentrated to give a residue, which was treated with $NH_4OAc$ (42 mg, 0.64 mmol) in $2N\ NH_3$ in EtOH (10 mL) at rt for 16 hours. After the mixture was concentrated, the residue was purified by HPLC to give the title compound (45 mg, 61%). By using general Pinner reaction conditions, 1N-(2'-tert-butylaminosulfonyl-[1,1'] biphenylamino)carbonylmethyl-5-cyanobenzimidazolinone (0.24 mmol) was converted to its amidino derivative (60 mg, 54%). For Example 1: $^1H$ NMR $(CD_3OD)$ δ 8.08 (dd, J=8.5 Hz, J=1.5 Hz, 1H), 7.62 (dt, J=8.5 Hz, J=1.5 Hz, 2H), 7.59–7.55 (m, 3H), 7.50 (td, J=7.8 Hz, J=1.5 Hz, 1H), 7.39 (dt, J=8.4 Hz, J=1.5 Hz, 2H), 7.31 (dd, J=7.3 Hz, J=1.4 Hz, 1H), 7.27 (d, J=8.8 Hz, 1H), 4.82 (s, 2H); $^{13}C$ NMR $(CD_3OD)$ δ 168.44, 167.52, 156.97, 143.08, 141.54, 139.03, 137.37, 134.89, 133.66, 132.92, 132.70, 131.26, 128.73, 128.61, 123.56, 122.07, 120.58, 110.74, 108.96, 44.63; ESMS: 465 $(M+H)^+$; HRMS:(M+H) calcd. for $C_{22}H_{20}N_6O_4S_1$ 465.1345, found 465.1335; Anal.: $(C_{22}H_{18}N_4O_1+1.5TFA+0.08HCl+1H_2O)$ C, H, N, S, F, Cl. For Example 2: $^1H$ NMR $(CD_3OD)$: δ 8.09 (dd, J=7.8 Hz, J=1.2 Hz, 1H), 7.62 (d, J=8.8 Hz, 2H), 7.59–7.54 (m, 2H), 7.54–7.50 (m, 2H), 7.40 (dd, J=8.8 Hz, J=2.0 Hz, 2H), 7.33 (d, J=8.1 Hz, 2H), 4.86 (s, 2H); ESMS: 465.4 $(M+H)^+$.

Example 3

1N-[4'-(p-chlorophenyl)thiazolyl-2'-amino) carbonylmethyl-6- amidinobenzimidazolinone Preparation of 1N-[4'-(p-chlorophenyl)thiazolyl-2'- amino) carbonylmethyl-6-amidinobenzimidazolinone.

A mixture of 1N-Boc-5-cyano-benzoimidazolinone (210 mg, 0.81 mmol), 2-(2-chloroacetamido)-4-(p-chlorophenyl)-5- thiazole (255 mg, 0.89 mmol), and $K_2CO_3$ (138 mg, 1.0 mmol) in acetone (10 mL) was stirred at 68° C. for 18 hours. The mixture was diluted with EtOAc (150 mL), washed with water and brine, and dried over $MgSO_4$. Concentration gave a crude product, which underwent a Pinner reaction, followed by HPLC purification, to give the product (150 mg, 43.3% for the two steps). $^1H$ NMR $(CD_3OD)$ δ 7.88 (d, J=8.4 Hz, 2H), 7.56 (d, J=8.4 Hz, 1H), 7.53 (s, 1H), 7.41 (s, 1H), 7.38 (d, J=8.5 Hz, 2H), 7.30 (d, J=8.1 Hz, 1H), 4.93 (s, 2H); $^{13}C$ NMR $(CD_3OD)$ δ 168.51, 167.09, 159.04, 156.88, 150.20, 136.79, 134.66, 134.55, 130.31, 129.76, 128.53, 123.70, 123.17, 122.65, 109.89, 109.49, 109.81, 44.01; ESMS: m/z 427.2 $(M+H)^+$; HRMS: (M+H) calcd. for $C_{19}H_{15}N_6O_2S_1Cl_1$ 427.0744, found 427.0743; Anal.: ($C_{19}H_{15}N_6O_2S_1Cl_1$+1.57TFA+0.22HCl+ $3H_2O$) C, H, N, S, F, Cl.

Example 4

5-Amidino-1N-(1'N-(4'- benzylpiperidino) carbonylmethyl)benzimidazolinone

Preparation of 1N-(4-benzylpiperidino) carbonylmethylchloride.

A solution of 4-benzylpiperidine (17.5 g, 100 mmol) in THF (250 mL) was treated with $K_2CO_3$ (14 g, 101 mmol) and chloroacetylchloride (11.3 g, 100 mmol) at rt for 2 hours. The reaction mixture was filtered. The filtrate was concentrated, and then dissolved in EtOAc and water. The 25 organic layer was washed with brine, dried over $MgSO_4$, and concentrated to give the product (21.6 g, 91.5%). $^1H$ NMR ($CDCl_3$) δ 7.32–7.12 (m, 5H), 4.09 (s, 2H), 3.79–3.76 (m, 2H), 2,56 (d, J=7.0 Hz, 2H), 1.89–1.80 (m, 1H), 1.79–1.71 (m, 4H), 1.28–1.12 (m, 2H).

Preparation of N-(4-benzylpiperidino) carbonylmethylamine.

To a solution of 1N-(4- benzylpiperidino) carbonylmethylchloride (3.3 g, 14 mmol) in acetone (48 mL) and water (32 mL) was added $NaN_3$ (1.4 g, 21 mmol), and the resulting mixture was refluxed for 16 hours.

The mixture was concentrated, and the resulting aqueous solution was extracted with EtOAc. The organic layer was dried over $MgSO_4$ and concentrated to give an azide intermediate as an oil. The oil was dissolved in MeOH (200 mL) and treated with hydrogen in the presence of 5% Pd on carbon for 16 hours. The mixture was filtered, and the filtrate was concentrated to give the desired product (2.8 g, 82% for the two steps) as a colorless oil. $^1H$ NMR ($CDCl_3$) δ 7.28 (d, J=7.8 Hz, 2H), 7.20 (dd, J=7.3 Hz, J=7–0 Hz, 1H), 7.13 (d, J=7.0 Hz, 2H), 4.59 (d, J=10.3 Hz, 1H), 3.74–3.61 (m, 1H), 3.46 (d, J=14.6 Hz, 2H), 2.89 (t, J - 12.4 Hz, 1H), 2.59–2.54 (m, 2H), 1.91–1.68 (m, 6H), 1.17–1.13 (m, 2H); MS(CI) m/z 233 (M+H).

Preparation of 4-cyano-2-nitro-1N-(1'N-(4-benzylpiperidino)carbonylmethyl)aniline.

A solution of 4-cyano-2-nitro-benzenechloride (1,82 g, 10 mmol), 1N-(4-benzylpiperidino)carbonylmethylamine (2 g, 8.6 ; mmol) and $NaHCO_3$ (0.84 g, 10 mmol) in DMF (10 mL) was stirred at 100° C. for 16 hours. The mixture was cooled to rt, diluted with EtOAc (150 mL), and filtered. The residue was washed with water and EtOAc, and dried by air to give the product (1.6 g, 49.2%) as a golden solid. The filtrate was washed with 1N HCl, water and brine, dried over $MgSO_4$, and concentrated to give more of the same product (1.1 g, 29%). $^1H$ NMR ($CDCl_3$) δ 9.33 (s, 1H), 8.55 (d, J=1.5 Hz, 1H), 7.63 (d, J=8.8 Hz, 1H), 7.33–7.20 (m, 3H), 7.14 (d, J=7.0 Hz, 2H), 6.78 (d, J=9.1 Hz, 1H), 4.65 (d, J=13.5 Hz, 1H), 4.07 (d, J=3.7 Hz, 2H),3.71 (d, J=12.8 Hz, 1H), 3.07 (t, J=12.8 Hz, 1H), 2.67 (t, J=12.8 Hz, 1H), 2.58 (t, J=6.3 Hz, 2H), 1.85–1.95 (m, 3H), 1.22 (q, J=12.5 Hz, 2H); MS(CI) m/z 379 (M+H).

Preparation of 2-amino-4-cyano-1N-(1'N-(4'-benzylpiperidino)carbonylmethyl)aniline.

A solution of 4-cyano-2-nitro-1N-(1'N-(4'-benzylpiperidino)carbonylmethyl)aniline (1.6 g, 4,23 mmol) in MeOH (120 mL) was treated with hydrogen in the presence of 5% Pd on carbon (0.2 g) for 16 hours. The mixture was filtered, and the filtrate was concentrated, followed by purification by CC with $CH_2Cl_2$, to give the product (1.33 g, 90%). $^1H$ NMR ($CDCl_3$) δ 7.26–7.03 (m, 6H), 6.86 (d, J=1.5 Hz, 1H), 6.38 (d, J=8.1 Hz, 1H), 5.10 (bs, 1H), 4.54 (d, J=12.8 Hz, 1H), 3.86 (d, J=4.5 Hz, 2H),3.74 (s, 1H), 3.65 (d, J=12.8 Hz, 1H), 3,61 (s, 1H), 3.03 (t, J=12.8 Hz, 1H), 2.61 (d, J=12.8 Hz, 1H), 2.53–2.51 (m, 2H), 1.80–1.65 (m, 3H), 1.35–1.05 (m, 2H); MS(CI) m/z 349 (M+H).

Preparation of 5-cyano-1N-(1'N-(4'- benzylpiperidino) carbonylmethyl)-benzoimidazolinone.

A solution of 2-amino-4-cyano-1N-(1'N-(4'-benzylpiperidino)carbonylmethyl)aniline (320 mg, 0.94 mmol) in THF (10 mL) was treated with 1,1'-carbonyldiimidazole (162 mg, 1 mmol) at rt for 4 hours. The mixture was diluted with EtOAc (100 mL) and washed with brine (50 mL). The organic layer was dried over $MgSO_4$ and concentrated to give a crude, which was purified on TLC plates with 20% EtOAc in $CH_2Cl_2$ to give the product (303 mg, 86.2%). $^1H$ NMR ($CDCl_3$) δ 7.38–7.12 (m, 7H), 6.96 (d, J=8.1 Hz, 1H), 4.69 (dd, J=24.2 Hz, J=16.8 Hz, 2H), 4.55 (d, J=13.2 Hz, 1H), 3.92 (d, J=13.5 Hz, 1H),3.49 (s, 1H), 3.11 (t, J=13.2 Hz, 1H), 2.61–2.58 (m, 3H), 1.83–1.72 (m, 3H), 1,26–1.21 (m, 2H); MS(CI) m/z 375.3 (M+H).

Preparation of 5-amidino-1N-(1'N-(4,- benzylpiperidino) carbonylmethyl)-benzoimidazolinone.

By using of Pinner conditions followed by purification on HPLC, 5-cyano-1N-(1,N-(4'- benzylpiperidino) carbonylmethyl)benzoimidazolinone (300 mg, 0.8 mmol) was converted to the product (195 mg, 62.5%). $^1H$ NMR ($CD_3OD$) δ 7.54 (dd, J=8.3 Hz, J=2.0 Hz, 1H), 7.51 (d, J=1.7 Hz, 1H), 7.29–7.14 (m, 6H), 4.94 (d, J=17.1 Hz, 1H), 4.85 (d, J=17.1 Hz, 1H), 4.42 (d, J=13.2 Hz,1H), 4.02 (d, J=13.7 Hz, 1H),3,12 (td, J=13.4 Hz, J=2.3 Hz, 1H), 2.64 (td, J=13.3 Hz, J=2.3 Hz, 1H), 2.58 (d, J=7.1 Hz, 2H), 1.93–1.81 (m, 1H), 1,78 (d, J=13.4 Hz, 1H), 1.68 (d, J 12.7 Hz, 1H), 1.39–1.29 (qd, J=12.7 Hz, J=4.0 Hz, 1H), 1.15 (qd, J=12.7 Hz, J=4.0 Hz, 1H); MS(ES) m/z 392.3 (M+H); HRMS:(M+ H) calcd. for $C_{22}H_{25}N_5O_2$ 392.2087, found 392.2071; Anal.: ($C_{22}H_{25}N_5O_2$+1.0TFA+0.07HCl).

Example 5

1N-(2'-Aminosulfonyl-[1,1']biphenylamino) carbonylmethyl-3N-p- hydroxyethylene-6-amidinobenzimidazolinone Preparation of 3-amino-4N-(β- hydroxyethylene) aminobenzonitrile.

A solution of 4-chloro-3-nitrobenzonitrile (18.3 g, 100 mmol), β-hydroxyethyleneamine(15 g, 245 mmol) and $NaHCO_3$ (8.4 g, 100 mmol) in MeOH (200 mL) was refluxed for 16 hours. The mixture was treated with hydrogen gas in the presence of 10% Pd on carbon (0.5 g) in MeOH (20 mL) for two days. The reaction mixture was filtered, and the filtrate was concentrated. The resulting residue was partitioned in EtOAc and water. The organic layer was neutralized with 1N HCl to pH 7, and then washed with brine, dried over $MgSO_4$, and concentrated to give the product (16 g, 90.4% for the two steps). MS(CI) m/z 178 (M+H); $^1H$ NMR ($CD_3OD$) δ 7.00 (dd, J T 8.4 Hz, J=1.8 Hz, 1H), 6.89 (d, J=2.2 Hz, 1H), 6.58 (d, J=8.4 Hz, 1H), 3.75 (t, J=5.6 Hz, 2H), 3.28 (t, J=5.5 Hz, 2H).

Preparation of 1N-β-hydroxyethylene-5-cyanobenzoimidazolinone.

After a solution of 3-amino-4N-(β- hydroxyethylene) aminobenzonitrile (6 g, 33.7 mmol) in THF (300 mL) was added slowly into a solution of 1,1'- carbonyldiimidazole (6 g, 37 mmol) in THF (200 mL), the resulting mixture was stirred at rt for 24 hours. The mixture was concentrated and the residue was dissolved in EtOAc (300 mL) and water (100 mL). The organic layer was washed with 1N HCl (50 mL), water (50 mL×2) and brine (30 mL×2), dried over $MgSO_4$, and concentrated to give the product (5.9 g, 100%). MS(CI) m/z 204 (M+H); $^1H$ NMR ($CD_3OD$) δ 7.26 (dd, J=8.4 Hz, 1H), 7.09 (d, J=1.5 Hz, 1H), 6.94 (dd, J=8.1 Hz, J=1.8 Hz, 1H), 4.53 (t, J=8.0 Hz, 2H), 3.93 (t, J=8.0 Hz, 2H).

Preparation of 1N-(21-aminosulfonyl-[1,1']-biphenylamino)carbonylmethyl-3N-β-hydroxyethylene-6-amidinobenzimidazolinone.

To a solution of 1N-β-hydroxyethylene-5- cyanobenzoimidazolinone (100 mg, 0.5 mmol) in acetone (5 mL) was added $K_2CO_3$ (138 mg, 1 mmol), NaI (75 mg, 0.5 mmol), and N-(2'-tert-butylaminosulfonyl-[1,1']-biphenylamino)-carbonylmethylchloride (190 mg, 0.5 mmol). After being refluxed for 16 hours, the mixture was diluted with EtOAc (100 mL), washed with water (×2) and brine (×2), dried over $MgSO_4$, and concentrated to give a crude product of the nitrile intermediate. The nitrile was directly carried out in a Pinner reaction, followed by HPLC purification, to give the title compound (130 mg, 51% for the two steps). $^1$H NMR ($CD_3OD$) δ 8.08 (dd, J=7.7 Hz, J=1.1 Hz, 1H), 7.63 (d, J=8.4 Hz, 2H), 7.59–7.45 (m, 5H), 7.38 (d, J=8.4 Hz, 2H), 7.33 (dd, J=4.0 Hz, J=1.5 Hz, 1H), 7.31 (d, J=4.0 Hz, 1H), 4.62 (t, J=7.7 Hz, 2H), 4.13 (s, 2H), 4.09 (t, J=7.7 Hz, 2H); ESMS: m/z 509.4 (M+H)$^+$.

Example 6

1N-(1'N-(2'-aminosulfonyl-[1,1']- biphenylamino) carbonylmethyl)-6-amidinobenzoxazolinone Preparation of 3-amino-4-hydroxybenzonitrile.

A solution of 4-hydroxy-3-nitrobenzonitrile (10 g, 61 mmol) in MeOH (200 mL) was treated with hydrogen gas through a balloon in the presence of 5% Pd on active carbon (0.5 g) at room temperature for 24 hours. The mixture was filtered, and the filtrate was concentrated to give the product (8.2 g, 100%).

Preparation of 6-cyanobenzoxazolinone.

To a solution of 3-amino-4-hydroxybenzonitrile (8.2 g, 61 mmol) in THF (200 mL) was added 1,1'-carbonyldiimidazole (11.6 g, 72 mmol) and the resulting mixture was stirred at room temperature for 16 hours. The reaction was then quenched with 1N HCl (50 mL), and the mixture was extracted with EtOAc (200 mL). The organic layer was washed with brine, dried over $MgSO_4$, and concentrated to give 6-cyanobenzoxazolinone (9.8 g, 100%). $^1$H NMR ($CDCl_3$) δ 7.49 (dd, J=8.4 Hz, J=1.5 Hz, 1H), 7.34 (d, J=1.5 Hz, 1H), 7.31 (d, J=8.4 Hz, 1H), 7.15 (d, J=0.9 Hz, 1H).

Preparation of 1N-(1'N-(2'-aminosulfonyl-[1,1']-biphenylamino)carbonylmethyl-6-amidinobenzoxazolinone.

A mixture of 6-cyanobenzoxazolinone (160 mg, 1 mmol), 1N- (2'-tert-butylaminosulfonyl-[1,1']- biphenylamino) carbonylmethylene chloride (380 mg, 1 mmol), NaI (75 mg, 0.5 mmol), and $K_2CO_3$ (207 mg, 1.5 mmol) in acetone (10 mL) was refluxed for 4 hours. The mixture was neutralized with 1N HCl to pH 7 and extracted with EtOAc (200 mL). The organic layer was washed with brine, dried over $MgSO_4$, and concentrated to give a crude. The crude underwent a Pinner reaction, followed by HPLC purification, to give the title product (232 mg, 50%). $^1$H NMR ($CD_3OD$) δ 8.12 (dd, J=7.7 Hz, J=1.8 Hz, 1H), 7.92 (d, J=1.2 Hz, 1H), 7.69 (td, J 7.7 Hz, J=2.2 Hz, 1H), 7.62 (dd, J=7.3 Hz, J=1.1 Hz, 1H), 7.57 (d, J=8.4 Hz, 2H), 7.51 (d, J=8.4 Hz, 2H), 7.36 (dd, J=7.8 Hz, J=1.6 Hz, 2H), 7.15 (d, J=8.4 Hz, 1H), 4.60 (s, 2H); $^{13}$C NMR (DMSO-$d_6$) δ 169.12, 164.26, 158.60, 154.17, 142.25, 139.74, 139.01, 132.49, 131.54, 131.17, 129.75, 129.50, 127.93, 127.33, 125.52, 123.78, 118.42, 117.24, 51.69; ESMS: m/z 466.4 (M+H)$^+$; HRMS: (M+H) calcd. for $C_{22}H_{20}N_5O_5S_1$ 466.1185, found 466.1157.

Example 7

1N-(N-p-(4'-oxazolyl)phenylamino)carbonylmethyl-6-amidino- benzoxazolinone

Preparation of 1N-[N-p-(4'- oxazolyl)phenylamino) carbonylmethyl-6-cyano-benzoxazolinone.

A mixture of 6-cyanobenzoxazolinone (160 mg, 1 mmol), p- (4-oxazolyl)phenyl chloroacetamido (380 mg, 1 mmol), NaI (150 mg, 1 mmol), and $K_2CO_3$ (138 mg, 1 mmol) in acetone (10 mL) was refluxed for 24 hours and then quenched with water (10 mL). The mixture was filtered, and the residue was collected and dried to give a crude product (400 mg). $^1$H NMR ($CDCl_3$) δ 7.91 (s, 1H), 7.67 (d, J=8.4 Hz, 2H), 7.63 (d, J=1.8 Hz, 1H), 7.45 (d, J=8.8 Hz, 2H), 7.37 (dd, J=8.8 Hz, J=1.8 Hz, 1H), 7.29 (s, 1H), 6.90 (d, J=8.4 Hz, 1H), 4.44 (s, 2H).

Preparation of 1N—(N-p-(4'- oxazolyl)phenylamino) carbonylmethyl-6-amidino-benzoxazolinone.

A crude of 1N-(N-p-(4'- oxazolyl)phenylamino) carbonylmethyl-6-cyano-benzoxazolinone (1 mmol) was carried on in a Pinner reaction, followed by purification by HPLC, to give the product (100 mg, 26.5%): $^1$H NMR ($CD_3OD$) δ 8.28 (s, 1H), 7.90 (d, J=2.6 Hz, 1H), 7.87 (d, J=8.8 Hz, 2H), 7.69 (dd, J=8.8 Hz, J=2.2 Hz, 1H), 7.61 (d, J=8.6 Hz, 2H), 7.60 (s, 1H), 7.13 (d, J=8.8 Hz, 1H), 4.57 (s, 2H); ESMS: m/z 378 (M+H)$^+$; Anal.: ($C_{19}H_{15}N_5O_4$+ 0.4TFA+0.85HCl+3$H_2O$)

Example 8

1N((1'N-(4'N-benzylsulfonylpiperazino) carbonylmethyl-6- amidino-benzoxazolinone Preparation of N-benzylsulfonylpiperazine.

Acylation of N-Boc-piperazine (1.86 g, 10 mmoL) with benzylsulfonyl chloride (1.9 g, 10 mmol) in $CH_3CN$ (20 mL) in the presence of $Na_2CO_3$ (1.01 g, 12 mmol) was carried out at rt for 16 hours. The mixture was diluted with EtOAc (150 mL), washed with water (50 mL), dried over $MgSO_4$, and concentrated to give 1N-Boc-4N-benzylsulfonyl-piperazine (3.3 g, 98%). $^1$H NMR ($CDCl_3$) δ 7.39 (bs, 5H), 4.23 (s, 2H), 3.38–3.35 (m, 4H), 3.07–3.05 (m, 4H), 1.44 (s, 9H). The Boc-intermediate was deprotected with 4M HCl in dioxane (20 mL) at rt for 1 hour. The mixture was diluted with EtOAc, washed with 1N NaOH and water, dried over $MgSO_4$, and concentrated to give the product (1.9 g, 81%). $^1$H NMR ($CDCl_3$) δ 7.46–7.43 (bs, 5H), 4.22 (s, 2H), 3.11–3.08 (m, 4H), 2.83–2.79 (m, 4H).

Preparation of N-benzylsulfonylpiperazino-2-chloroacetamido.

Acylation of N-benzylsulfonyl-piperazine (1.9 g, 7.9 mmoL) with chloroacetyl chloride (1.13 g, 10 mmol) in $CH_3CN$ (20 mL) in the presence of $Na_2CO_3$ (10 mmol) was carried out at rt for 2 hours. The mixture was diluted with EtOAc, washed with water, dried over $MgSO_4$, and concentrated to give the product (2.34 g, 95%). $^1$H NMR ($CDCl_3$) δ 7.39 (bs, 5H), 4.26 (s, 2H), 4.02 (s, 2H), 3.58 (t, J=4.8 Hz, 2H), 3.45 (t, J=4.8 Hz, 2H), 3.14–3.11 (m, 4H).

Preparation of 1N-(1,N-(4'N- benzylsulfonylpiperazino) carbonylmethyl-6-amidino- benzoxazolinone.

A mixture of 6-cyanobenzoxazolinone (80 mg, 0.5 mmol), N- benzylsulfonylpiperazino-2-chloroacetamido (158 mg, 0.5 mmol), and $K_2CO_3$ (138 mg, 1 mmol) in acetone (5 mL) was refluxed for 5 hours. The mixture was diluted with EtOAc, washed with water, and dried over $MgSO_4$. Concentration gave a crude, which was purified on TLC plates to give the cyano precursor. The cyano precursor was carried on in a Pinner reaction, followed by purification by HPLC, to give the product (56 g, 20% for two steps). $^1$H NMR (DMSO-d$_6$) δ 9.31 (bs, 1.5H), 9.07 (bs, 1.5H), 7.69 (d, J=1.5 Hz, 1H), 7.64 (d, J=8.3 Hz, 1H), 7.59 (dd, J=8.8 Hz, J=1.8 Hz, 1H), 7.44–7.37 (m, 5H), 4.90 (s, 2H), 4.48 (s, 2H), 3.57 (bs, 2H), 3.47 (bs, 2H), 3.24 (bs, 2H), 3.15 (bs, 2H); $^{13}$C NMR (DMSO-d$_6$) δ 165.26, 163.88, 153.90, 145.37, 132.03, 130.94, 129.31, 128.43, 128.30, 124.17, 123.29, 110.11, 109.43, 54.79, 45.38, 45.08, 44.14, 43.35, 41.62, 40.41; ESMS: m/z 458.2 (M+H)$^+$: HRMS: (M+H) calcd. for C$_{21}$H$_{24}$N$_5$O$_5$S$_1$ 458.1498, found 458.1516.

Example 9

7-amidino-1N-(4-bromophenyl)carbonylmethyl-3,4-dihydroquinoxalin-2(1H)-one

Preparation of 7-cyano-3,4-dihydroquinoxalin-2(1H)-one.

To a solution of 4-chloro-3-nitrobenzonitrile (18.3 g, 100 mmol) and glycine methyl ester•hydrochloride (12.3 g, 100 mmol) in EtOH (150 mL) was added NaHCO$_3$ (25.2 g, 300 mmol), and the resulting mixture was refluxed for 16 hours. The mixture was filtered and the filtrate was concentrated. The resulting residue was partitioned in EtOAc and water. The organic layer was neutralized with 1N HCl to pH 7 and then washed with brine, dried over MgSO$_4$, and concentrated to give a crude (25 g). A solution of the crude was hydrogenated in MeOH (500 mL) in the presence of 10% Pd on carbon (1.5 g) at room temperature for 6 hours. The mixture was filtered and the filtrate was concentrated to give more of the same product (19.5 g, 100%). $^1$H NMR (DMSO-d$_6$) δ 10.50 (s, 1H), 7.15 (dd, J=8.1 Hz, J=1.8 Hz, 1H), 6.94 (d, J=1.6 Hz, 1H), 6.93 (s, 1H), 6.68 (d, J=8.4 Hz, 1H), 3.90 (d, J=1.1 Hz, 2H); MS(CI) m/z 191 (M+NH$_4$).

Preparation of 7-cyano-1N-(p-bromophenyl) carbonylmethyl-3,4- dihydroquinoxalin-2(1H)-one.

To a solution of 7-cyano-3,4-dihydroquinoxalin-2(1H)-one (4 mg, 20 mmol) in THF (100 mL) was added K$_2$CO$_3$ (152 mg, 1.1 mmoL), 18-crown-6 (230 mg), and 2,4'-dibromoacetophenone (5.54 g, 20 mmol), and the resulting mixture was stirred for 16 hours. The mixture was diluted with EtOAc and filtered. The residue was washed with EtOAc and water, and dried by air to give the product (2.8 g, 37.8%). The filtrate was washed with brine (50 mL×4), dried over MgSO$_4$, and concentrated to give a crude material, which was recrystallized in EtOAc (20 mL) to give the product (2 g, 27%) as a white solid. $^1$H NMR (DMSO-d$_6$) δ 8.02 (d, J=8.4 Hz, 2H), 7.83 (d, J=8.4 Hz, 2H), 7.35 (d, J=1.4 Hz, 1H), 7.26 (dd, J=8.1 Hz, J=1.4 Hz, 1H), 7.10 (s, 1H), 6.81 (d, J=8.4 Hz, 1H), 5.50 (s, 2H), 4.05 (d, J=1.1 Hz, 2H); MS(CI) m/z 370/372 (M+H).

Preparation of 7-amidino-1N-(4'-bromophenyl)carbonylmethyl- 3,4-dihydroquinoxalin-2 (1H)-one.

MP: 145–150° C.; MS(ES): m/z 385/387 (M+H); HRMS: (M+H) calcd. for C$_{17}$H$_{15}$N$_4$O$_2$Br$_1$ 389.0436, found 389.0418; Anal. (C$_{17}$H$_{15}$N$_4$O$_2$Br$_1$+1TFA+HCl) C, H, N, F, Cl; $^1$H NMR (CD$_3$OD) δ 8.02 (d, J=8.4 Hz, 2H), 7.76 (d, J=8.4 Hz, 2H), 7.40 (dd, J=8.4 Hz, 1H), 7.11 (d, J=2.2 Hz, 1H), 6.87 (d, J=8.4 Hz, 1H), 5.50 (s. 2H), 4.10 (S, 2H).

Example 10

7-amidino-1N-(31-amino-[1,1']biphenyl)carbonyl-methyl-3,4- dihydroquinoxalin-2(1H)-one Preparation of 7-cyano-1N-(33-amino-[1,1']- biphenyl) carbonylmethyl-3,4-dihydroquinoxalin-2(1H)-one.

A mixture of 7-cyano-1N-(p-bromophenyl) carbonylmethyl- 3,4-dihydroquinoxalin-2(1H)-one (370 mg, 1 mmol), 3- aminophenyoboronic acid (137 mg, 1 mmol), NaHCO$_3$ (210 mg, 2 mmol), and Pd(PPh$_3$)$_4$ (60 mg) in THF (10 mL) and water (1 mL) was refluxed under nitrogen for 16 hours. The mixture was filtered, and the residue was washed with water, CH$_2$Cl$_2$, and dried by air to give the product (310 mg, 81.6%). MS(ES): m/z 383.2 (M+H); $^1$H NMR (CD$_3$OD) δ 8.22 (d, J=8.4 Hz, 2H), 7.85 (d, J=8.4 Hz, 2H), 7.74 (d, J=8.1 Hz, 1H), 7.63–7.58 (m, 2H), 7. 34 (dd, J=8.4 Hz, J=1.4 Hz, 1H), 7.22 (dd, J=8.4 Hz, J=1.4 Hz, 1H), 7.01 (d, J=8.4 Hz, 1H), 6.81 (d, J=8.0 Hz, 1H),5.54 (s, 2H), 4.08 (s, 2H)

Preparation of 7-amidino-1N-(3'-amino-[1,1']- biphenyl) carbonylmethyl-3,4-dihydroquinoxalin-2(1H)-one.

By using the general procedure of Pinner reaction, followed by HPLC purification, the product (157 mg, 50%) was obtained from its cyano precursor (300 mg, 0.78 mmol). MP: 85° C.; MS(ES): m/z 200.8 (M+H)$^{2+}$; HRMS:(M+H) calcd. for C$_{23}$H$_{21}$N$_5$O$_2$ 400.1774, found 400.1780; $^1$H NMR (CD$_3$OD) δ 8.21 (d, J=8.4 Hz, 2H), 7.84 (d, J=8.4 Hz, 2H), 7.51–7.40 (m, 4H), 7.20–7.15 (m, 1H), 7.15 (dd, J=2.2 Hz, 1H), 6.88 (d, J=8.4 Hz, 1H),5.56 (s, 2H), 4.12 (s, 2H).

Example 11

7-amidino-1N-(41-fluoro-[1,1']biphenyl)carbonyl-methyl-3,4- dihydroquinoxalin-2(1H)-one Preparation of 7-cyano-1N-(4'-fluoro-[1,1']- biphenyl) carbonylmethyl-3,4-dihydroquinoxalin-2(1H)-one.

A mixture of 7-cyano-1N-(p-bromophenyl) carbonylmethyl- 3,4-dihydroquinoxalin-2(1H)-one (370 mg, 1 mmol), 4- fluorophenylboronic acid (137 mg, 1 mmol), NaHCO$_3$ (210 mg, 2 mmol), and Pd(PPh$_3$)$_4$ (60 mg) in THF (10 mL) and water (1 mL) was refluxed under nitrogen for 16 hours. The mixture was filtered, and the filtrate was diluted with EtOAc (100 mL). The organic layer was dried with MgSO$_4$, filtered, and concentrated to give a crude product (340 mg, 88.1%). MS (ES): m/z 386 (M+H); $^1$H NMR (CDCl$_3$) δ 8.13 (d, J=8.1 Hz, 2H), 7.73 (d, J=8.4 Hz, 2H), 7.63 (dq, J=8.8 Hz, J=2.3 Hz, 2H), 7.20 (d, J=8.4 Hz, 2H), 7.18 (d, J=8.4 Hz, 1H), 6.73 (d, J=8.4 Hz, 1H), 6.75 (s, 1H), 5.41 (s, 2H), 4.19 (s, 2H).

Preparation of 7-amidino-1N-(41-fluoro-[1,1']- biphenyl) carbonylmethyl-3,4-dihydroquinoxalin-2 (1H)-one.

By using Pinner conditions, followed by HPLC purification, the cyano precursor (300 mg, 0.80 mmol) was converted to the product (120 mg, 37%) MP: 138–140° C.; MS(ES): m/z 403 (M+H); $^1$H NMR (CD$_3$OD) δ 8.19 (d, J=8.4 Hz, 2H), 7.81 (d, J=8.4 Hz, 2H), 7.88 (d, J=8.4 Hz, 1H), 7.73 (dq, J=5.3 Hz, J=2.1 Hz, 2H), 7.41 (dd, J=8.4 Hz, J=2.3 Hz, 1H), 7.22 (td, J=8.4 Hz, J=2.2 Hz, 2H), 7.15 (d, J=2.2 Hz, 1H), 5.57 (s, 2H), 4.11 (s, 2H); $^{13}$C NMR (CD$_3$OD) δ 192.51, 165.72, 145.43, 142.16, 135.74, 133.37, 128.85, 128.74, 128.64, 127.38, 126.88, 124.34, 115.60, 115.32, 113.80, 113.21, 48.48, 45.51; Anal.: (C$_{23}$H$_{19}$N$_4$O$_2$F$_1$+1.2TFA+0.05HCl+1H$_2$O) C, H, N, F, Cl.

Example 12

7-amidino-1N-[1,1']-biphenylcarbonylmethyl-3,4-
Preparation of 7-amidino-1N-[1,1']- biphenylcarbonylmethyl-3,4- dihydroquinoxalin-2 (1H)-one.

A mixture of 7—cyano-1N-[(p-bromophenyl) carbonylmethyl- 3,4-dihydroquinoxalin-2(1H)-one (185 mg, 0.5 mmol), 4-phenyl- 2'-bromoacetophenone (137 mg, 0.5 mmol), K$_2$CO$_3$ (210 mg, 2 mmol), and 18-crown-6 (20 mg) in THF (10 mL) was stirred for 16 hours. The mixture was filtered, and the filtrate was diluted with EtOAc (100 mL). The organic layer was dried with MgSO$_4$, filtered, and concentrated to give a crude, which was carried on in a Pinner reaction, followed by HPLC purification, to give the product (120 mg, 37%) as a solid. MP: 148–150° C.; MS(ES): m/z 385.2 (M+H)$^+$; HRMS:(M+H) calcd. for C$_{23}$H$_{20}$N$_4$O$_2$ 385.1664, found 385.1650; 1H NMR (CD$_3$OD) δ 8.20 (d, J=8.4 Hz, 2H), 7.84 (d, J=8.0 Hz, 2H), 7.71 (d, J=7.4 Hz, 2H), 7.47 (d, J=7.7 Hz, 2H), 7.42–7.33 (m, 2H), 7.13 (d, J=1.8 Hz, 1H), 6.88 (d, J=8.4 Hz, 1H), 5.57 (s, 2H), 4.12 (s, 2H); 13C NMR (CD$_3$OD) δ 192.51, 165.72, 145.43, 142.16, 135.74, 133.37, 128.85, 128.74, 128.64, 127.38, 126.88, 124.34, 115.60, 115.32, 113.80, 113.21, 48.48, 45.51; Anal.: (C$_{23}$H$_{19}$N$_4$O$_2$F$_1$+1.2TFA+0.05HCl+ 1H$_2$O) C, H, N, F, Cl.

Examples 13 and 14

7-amidino-1N-(2-tert-butylsulfonamido- [1,1'] biphenyl)carbonylmethyl-3,4-dihydroquinoxalin-2 (1H)-one (Example 13) and 7-amidino-1N-(2'-sulfonamido-[1,1']- biphenyl)-carbonylmethyl-3,4-dihyroquinoxalin-2(1H)-one (Example 14)

Preparation of 7-cyano-1N-(4'-sulfonamido-[1,1']-biphenyl)carbonylmethyl-3,4-dihydroquinoxalin-2(1H)-one.

A mixture of 7-cyano-1N-(p-bromophenyl) carbonylmethyl- 3,4-dihydroquinoxalin-2(1H)-one (370 mg, 1 mmol), o-tert- butylsulfonamidophenyoboronic acid (257 mg, 1 mmol), NaHCO$_3$ (210 mg, 2 mmol), and Pd(PPh$_3$)$_4$ (90 mg) in THF (20 mL) and water (2 mL) was refluxed under nitrogen for 16 hours. The mixture was filtered, and the filtrate was diluted with EtOAc (100 mL). The organic layer was dried with MgSO$_4$, filtered, and concentrated to give a crude, which was purified on TLC plates to give the product (340 mg, 67.7%). MS(ES): m/z 503 (M+H); $^1$H NMR (CDCl$_3$) δ 8.21 (dd, J=8.0 Hz, J=1.5 Hz, 1H), 8.13 (d, J=8.4 Hz, 2H), 7.71 (d, J=8.4 Hz, 2H), 7.64–7.53 (m, 2H), 7.32 (dd, J=8.4 Hz, J=1.5 Hz, 1H), 7.23 (dd, J=8.1 Hz, J=1.5 Hz, 1H), 6.77 (d, J=1.1 Hz, 1H), 6.74 (d, J=8.1 Hz, 1H), 5.30 (s, 2H), 4.21 (s, 2H), 3.63 (s, 1H), 1.08 (s, 9H).

Preparation of 7-amidino-1N-(2'-tert-butylsulfonamido-[1, 1']- biphenyl)-carbonylmethyl-3,4-dihydroquinoxalin-2 (1H)-one and 7-amidino-1N-(2'-sulfonamido-1,1']-biphenyl)carbonylmethyl- 3,4-dihydroquinoxalin-2(1H)-one.

By using the general procedure of Pinner reaction, followed by HPLC purification, the cyano precursor (340 mg, 0.67 mmol) was converted to Example 13 (80 mg, 23%) and Example 14 (120 mg, 38.7%), respectively. For Example 13: HRMS:(M+H) calcd. for C$_{27}$H$_{30}$N$_5$O$_4$S$_1$ 520.2019, found 520.2013; $^1$H NMR (CD$_3$OD) δ 8.16 (d, J=8.8 Hz, 2H), 8.12 (dd, J=1.4 Hz, J=1.4 Hz, 1H), 7.67–7.56 (m, 2H), 7.63 (d, J=8.4 Hz, 2H), 7.41 (dd, J=8.4 Hz, J=1.9 Hz, 1H), 7.33 (dd, J=7.7 Hz, J=1,4 Hz, 1H), 7.16 (d, J=1.8 Hz, 1H), 6.88 (d, J=8.4 Hz, 1H), 5.58 (s, 2H), 4.13 (s, 2H), 1.07 (s, 9H); Anal.: (C$_{27}$H$_{30}$N$_5$O$_4$S$_1$+1.1TFA+0.5H$_2$O) C, H, N, S, F, Cl; For Example 14: HRMS: (M+H) calcd. for C$_{23}$H$_{21}$N$_5$O$_4$S$_1$ 464.1379, found 464.1394; $^1$H NMR (CD$_3$OD) δ 8.16 (d, J=8.8 Hz, 2H), 8.11 (d, J=8.4 Hz, 1H), 7.62 (d, J=8.4 Hz, 2H), 7.65–7.58 (m, 2H), 7.41 (dd, J=8.4 Hz, J=2.2 Hz, 1H), 7.36 (dd, J=7.3 Hz, J=1,4 Hz, 1H), 7.16 (d, J=2.3 Hz, 1H), 6.88 (d, J=8.8 Hz, 1H), 5.58 (s, 2H), 4.13 (s, 2H); $^{13}$C NMR (CD$_3$OD) δ 194.11, 167.16, 147.52, 143.64, 143.11, 140.84, 135.23, 133.09, 132.95, 131.29, 129.44, 128.89, 128.71, 125.78, 116.77, 115.20, 114.66, 54.77, 47.04.

Example 15

1N-(2'-aminosulfonyl-[1,1']biphenylamino)carbonyl-methyl-7- amidino-3,4-dihydroquinoxalin-2(1H)-one Preparation of 1N-(2'-aminosulfonyl-[1,1']- biphenylamino) carbonylmethyl-7-amidino-3,4-dihydroquinoxalin- 2(1H)-one.

A mixture of 7-cyano-3,4-dihydroquinoxalin-2(1H)-one (173 mg, 1 mmol), K$_2$CO$_3$ (152 mg, 1.1 mmol), 18-crown-6 (15 mg), and 1N-(2'-tert-butylaminosulfonyl-[1,1']-biphenylamino)carbonylmethyl chloride (380 mg, 1 mmol) in DMF (5 mL) was stirred at 80° C. for 16 hours. The mixture was diluted with EtOAc, washed with brine (50 mL×4), dried over MgSO$_4$, and concentrated to give a crude of the nitrile compound, which underwent a Pinner reaction and HPLC purification, to give the product (210 mg, 44% for the two steps). ESMS: m/z 479.2 (M+H); HRMS:(M+H) calcd. for C$_{23}$H$_{23}$N$_6$O$_4$S$_1$ 479.1502, found 479.1491; $^1$H NMR (DMSO-d$_6$) δ 10 34 (s, 1H), 8.93 (s, 2H), 8.56 (s, 2H), 8.02 (d, J=7.8 Hz, 2H), 7.62–7.54 (m, 5H), 7.52 (td, J=7.8 Hz, J=1.5 Hz, 1H), 7.34 (d, J=8.4 Hz, 2H), 7. 15 (d, J=8.2 Hz, 1H), 5.18 (s, 1H), 4.80 (s, 2H), 4.06 (s, 2H), 3.51 (bs, 2H); $^{13}$C NMR (CD$_3$OD) δ 168.44, 167.52, 156.97, 143.08, 141.54, 139.03, 137.37, 134.89, 133.66, 132.92, 132.70, 131.26, 128.73, 128.61, 123.56, 122.07, 120.58, 110.74, 108.96, 44.63

Example 16

6-amidino-1N-[1,1'-biphenyl)carbonylmethyl-3,4-dihydroquinoxalin-2 (1H)-one

Preparation of 2N-Boc-amino-5-cyanophenylglycin ethyl ester.

To a solution of N-Boc-2-amino-5-cyanoaniline (4.66 g, 20 mmol) in DMF (80 mL) was added K$_2$CO$_3$ (2.76 g, 20 mmol), 18- crown-6 (0.3 g), and ethyl bromoacetate (3.5 g, 22 mmol). After the mixture was stirred at 70° C. for 16 hours, it was cooled to rt, diluted with EtOAc, washed with water, and dried over MgSO$_4$. Filtration and concentration, followed by purification by CC with 5% EtOAc in CH$_2$Cl$_2$, provided the product (2.4 g, 41%). $^1$H NMR (CDCl$_3$) δ 7.67 (d, J=8.4 Hz, 1), 7.15 (dd, i =8.1 Hz, J=1.8 Hz, 1H), 6.86 (d, J=1.8 Hz, 1H), 6.43 (bs, 1H), 4.29 (q, J=7.0 Hz, 2H), 3.87 (d, J - 5.5 Hz, 2H), 1.53 (s, 9H), 1.33 (t, J=7.0 Hz, 3H).

Preparation of 6-cyano-3,4-dihydroquinoxalin-2(1H)-one.

N-Boc-2-amino-5-cyanophenylglycin ethyl ester (2.6 g, 8.17 mmol) in MeOH (20 mL) was treated with 4M HCl in dioxane (20 mL) at rt for 16 hours. To the mixture was added Et$_2$O until no more solid appeared. The solid was collected, washed with Et$_2$O, and dried by air to give the product (1.4 g, 82%). $^1$H NMR (CD$_3$COCD$_3$) δ 7.02 (d, J=8.4 Hz, 1H), 7.00 (d, J=1.8 Hz, 1H), 6.95 (d, J=8.4 Hz, 1H), 3.89 (s, 2H).

Preparation of 6-amidino-1N-[1,1']-biphenylcarbonylmethyl-3,4- dihydroquinoxalin-2(1H)-one.

A mixture of 6-cyano-3,4-dihydroquinoxalin-2(1H)-one (171 mg, 0.82 mmol), 4-phenyl-2'-bromoacetophenone (277 mg, 1 mmol), K$_2$CO$_3$ (140 mg, 1 mmol), and 18-crown-6 (30 mg) in DMF (5 mL) was stirred for 16 hours. The mixture was diluted with EtOAc (160 mL) and water (40 mL). The organic layer was washed with brine, dried with MgSO$_4$, filtered, concentrated, and purified on TLC plates to give a 6-cyano-1N-(4'- phenylphenyl)carbonylmethyl-3,4-dihydroquinoxalin-2(1H)-one (110 mg, 37%). The cyano precursor was carried on in a Pinner reaction, followed by HPLC purification, to give the product (30 mg, 26%) as a solid. HRMS: (M+H) calcd. for C$_{23}$H$_{20}$N$_4$O$_2$ 385.1651, found 385–1652; $^1$H NMR (CD$_3$OD) δ 8.52 (s, !H), 8.19 (d, J=8.4 Hz, 2H), 7.84 (d, J=8.4 Hz, 2H), 7.71 (d, J=7.0 Hz, 2H), 7.51–7.41 (m, 3H), 7.15 (bs, 1H), 6.87 (d, J=8.4 Hz, 1H), 5.57 (s, 2H), 4.07 (s, 2H).

Example 17

1-N-[1,1']Biphenylcarbonyl)ethyl-6-amidinobenzoxazolinone

Preparation of 3-[1,1']-biphenyl-1,2-propen-3-one.

trans-Benzyl(chloro)bis-(triphenylphosphine)palladium (II) (0.24 mmol, 0.18 g) and vinyltributyl tin (47.31 mmol, 15 g) were added to a suspension of [1,1']-biphenylcarbonyl chloride (45.49 mmol, 9.82 g) in 30 mL chloroform. The reaction mixture was warmed to 60° C. for ca. 15 h. Then the reaction mixture was pourred into diethyl ether and washed with water and half saturated KF solution. The tin salts were filtered the organics were dried over MgSO$_4$ and concentrated in vacuo. The crude material was purified by standard chromatographic technique to give the product as a white solid. LRMS: m/z 209(M+H, 100). $^1$H NMR (CDCL$_3$,300 MHz) δ 8.50 (d, 2H), 7.71 (d, 2H), 7.63 (d, 2H), 7.45 (m, 3H), 7.20 (m, 1H), 6.49 (dd, 1H), 5.95 (dd, 1H).
Preparation of 1N-([1,1']-biphenylcarbonyl)ethyl-6- amidinobenzoxazolinone.

6—Cyanobenzoxazolinone (5.0 mmol, 0.80 g) was synthesized as previously described and added to a solution of 3-[1,1']- biphenyl-1,2-propen-3-one (5.0 mmol, 1.04 g) and triethylamine (10.00 mmol, 1.39 mL) in 40 mL acetonitrile. The reaction mixture was warmed from ambient temperature to 77° C. for 2 h. The reaction mixture was concentrated and placed under high vaccum to give the crude product. The crude material was used directly. LRMS: m/z 386 (M+NH4, 100). The 1N-[[1,1']- biphenylcarbonyl]ethyl-6-cyanobenzoxazolinone was converted to its corresponding benzamidine via the Pinner synthesis and amidination with ammonium carbonate to give crude 1N-[4- biphenylcarbonyl]ethyl-6-amidinobenzoxazolinone. The crude product was purified by standard reverse phase HPLC. LRMS: m/z 386(M+H,100). HRMS: calcd for C$_{23}$H$_{20}$N$_3$O$_3$, 386.150467; found, 386.150040.

Example 18

1-([1,1']-Biphenylcarbonyl)ethyl-6-amidino-3N-methylbenzimidazolinone

6—Cyano-3N-methylbenzimidazolone (2.31 mmol, 0.40 g) which was synthesized similarly to its benzimidazolone analog except that 1N-methyl-2-amino-4-cyanoaniline was used as starting material and 3-(4-biphenyl)-1,2-propen-3-one (2.31 mmol, 0.48 g) were combined in 20 mL of acetonitrile to form a suspension. The reaction mixture was warmed to 77° C. and heated for 24 h. The reaction mixture was concentrated and the resulting residue was purified by standard chromatographic technique to give 1-(4-biphenylcarbonyl)ethyl-6- cyanobenzimidazolinone. LRMS: m/z 382(M+H,100). The purified material was subjected to Pinner conditions followed by reaction with ammonium carbonate to give the title compound 1-(4-biphenylcarbonyl) ethyl-6-amidino-3N- methylbenzimidazolinone. $^1$H NMR(CDCL$_3$,300 MHz): δ 9.12 (bs, 2H), 8.77 (bs, 2H), 8.01 (d, 2H), 7.78 (m, 3H). 7.72 (d, 2H), 7.43 (complex, 5H), 4.21 (t, 2H), 3.56 (t, 2H), 3.35 (s, 3H). LRMS: m/z 399.4(M+H,100). HRMS: calcd for C$_{24}$H$_{23}$N$_4$O$_2$, 399.182101; found, 399.181375.

Example 19

1-(1,1']-biphenylcarbonyl)ethyl-6-amidinobenzimidazolinone

6—Cyano-3N-acetylbenzimidazolone (1.47 mmol, 0.29 g) which was synthesized similarly to its benzimidazolone analog except that 1N-acetyl-2-amino-4-cyanoaniline was used as starting material and 3-(4-biphenyl)-1,2-propen-3-one (1.37 mmol, 0.29 g) were combined in 15 mL of acetonitrile to form a suspension. The reaction mixture was warmed to 77° C. and heated for 24 h. The reaction mixture was concentrated and the resulting residue was purified by standard chromatographic technique to give crude 1-(4-biphenylcarbonyl)ethyl-6-cyano-3N-acetylbenzimidazolinone. The crude material was subjected to Pinner conditions followed by reaction with ammonium carbonate to give the title compound 1-(4- biphenylcarbonyl)ethyl-6-amidinobenzimidazolinone. LRMS: m/z 385 (M+H,100). HRMS: calcd for C$_{23}$H$_{21}$N$_4$O$_2$, 385.166451; found, 385.167149.

Example 20

1N-(4-Bromophenylcarbonyl)ethyl-6-amidinabenzoxazolinone

Preparation of 1N-(4-Bromophenylcarbonyl)ethyl-6-cyanobenzoxazolinone.

6—Cyanobenzoxazolinone (7.06 mmol, 1.13 g) was synthesized as previously described (Example 6) and added to a solution of 4-bromo-beta-chloropropiophenone (7.77 mmol, 1.92 g) and triethylamine (17.66 mmol, 2.46 mL) in 100 mL acetonitrile. The reaction mixture was warmed to 77° C. for 24 h. The reaction mixture was allowed to cool to ambient temperature at which time the product precipitated from the solution as a white solid. LRMS: m/z 390(M+NH4). The 1N-(4- bromophenylcarbonyl)ethyl-6-cyanobenzoxazolinone was used directly and was converted to its corresponding benzamidine via the Pinner synthesis followed by amidination with ammonium carbonate to give crude 1N-(4-bromophenylcarbonyl)ethyl-6-amidinobenzoxazolinone. The crude product was purified by standard reverse phase HPLC. $^1$H NMR(dmso-d$_6$,300 MHz): δ 9.30 (bs, 2H), 9.10 (bs, 2H), 7.85 (m, 4H), 7.71 (d, 2H), 7.58 (s, 1H), 4.15 (t, 2H), 3.58 (t, 2H). LRMS: m/z 390(M+H,100). HRMS: calcd for C$_{17}$H$_{14}$BrN$_3$O$_3$, 388.029678; found, 388.030885.

Example 21

1N-14-(2-Aminosulfonylphenyl)pyridin-2-yl] aminocarbonylmethyl- 6-amidinobenzoxazolinone
Preparation of 2-Aminocarbonylmethylchloro-4-(2'-tert-butylsulphonylphenyl)pyridine.

Chloroacetyl chloride (8.23 mmol, 0.66 mL) was dripped into a solution of 2-amino-5-(2'-tert- butylsulphonylphenyl)pyridine (8.23 mmol, 2.51 g) in 80 mL THF. The reaction mixture was stirred overnight at ambient temperature. The reaction mixture was concentrated under reduced pressure to give 2-aminocarbonylmethylchloro-5-(2'- tert-butylsulphonylphenyl)pyridine as white solid. LRMS: m/z 382(M+H).
Preparation of 1N-[4-((2'-tert- Butylaminosulphonylphenyl)pyridin-1-yl)aminocarbonylmethyl]-6- amidinobenzoxazolinone.

6—Cyanobenzoxazolinone (5.33 mmol, 0.85 g) was added to a solution of 2-aminocarbonylmethylchloro-5-(2'-tert- butylaminosulphonylphenyl)pyridine (5.33 mmol, 2.22 g), sodium iodide (2.67 mmol, 0.40 g) and triethylamine (15.99 mmol, 2.23 mL) in 50 mL THF. The reaction mixture was warmed to reflux temperature for 24 h. Then the reaction mixture was concentrated and purified via standard flash chromotographic technique to give 1N-[4-((2'-tert-butylaminosulphonylphenyl)pyridin-1-yl) aminocarbonylmethyl]-6- cyanobenzoxazolinone. LRMS: m/z 506 (M+H,100). The 1N-[4- ((2'-tert-butylaminosulphonylphenyl)pyridin-1-yl)aminocarbonylmethyl]-6-cyanobenzoxazolinone was converted to its corresponding benzamidine via the Pinner synthesis and amidination with ammonium carbonate to give crude 1N-[5-((2'- tert-butylsulphonylphenyl)pyridin-1-yl)aminocarbonylmethyl]-6- amidinobenzoxazolinone. The crude product was purified by standard reverse phase HPLC. $^1$H NMR (DMSO-d$_6$, 300 MHz): δ 11.21 (s, 1H), 9.26 (s, 2H), 8.91 (s, 2H), 8.30 (d, 1H), 7.98 (m, 2H), 7.77 (m, 2H), 7.62 (m, 3H), 7.36 (m, 2H), 4.82 (bs, 2H). LRMS: m/z 467(M+H). HRMS: calcd for C$_{21}$H$_{17}$N$_6$O$_4$, 467.113765; found, 467.114384.

Example 22

1N-(4-Morpholinosulfonamidophenyl) aminocarbonylmethyl-6- amidinobenzoxazolinone Preparation of 4-Nitrobenzenemorpholinosulfonamide.

Morpholine (44.31 mmol, 3.86 mL) was dripped into a cooled (0° C.) solution of 4-nitrobenzenesulfonyl chloride (14.77 mmol, 3.27 g) in 100 mL methylene chloride. The reaction mixture was allowed to warm to ambient temperature overnight. Then the reaction mixture was concentrated under reduced pressure and diluted with EtOAC. The organics were washed 3×50 mL water, dried over MgSO$_4$ and concentrated in vacuo to give a yeloow solid. The crude 4-nitrobenzenemorpholinesulfonamide was used directly after a few hours under high vacuum. LRMS: m/z 290(M+NH4). The crude nitro compound was reduced catalytically with 10% palladium on carbon at 1 atm of hydrogen to give 0.43 g of crude 4- morpholinesulfonamidoaniline. LRMS: m/z 243 (M+H,100).

Preparation of 4- Aminocarbonylmethylchlorobenzenemorpholinosulfonamide.

Chloroacetyl chloride (1.78 mmol, 0.14 mL) was dripped into a solution of 4-morpholinesulfonamidoaniline (1.78 mmol, 0.43 g) and triethylamine (3.73 mmol, 0.52 mL) in 100 mL THF. The reaction mixture was stirred for 20 h at ambient temperature. The reaction mixture was concentrated under reduced pressure and worked up with water and brine washings to give the crude 4- aminocarbonylmethylchlorobenzenemorpholinesulfonamide. LRMS: m/z 319 (M+H).

Preparation of 1N-(4- Morpholinosulfonamidophenyl) carbonylmethyl-6- amidinobenzoxazolinone.

6—Cyanobenzoxazolinone (0.82 mmol, 0.13 g) was added to a solution 4- aminocarbonylmethylchlorobenzenemorpholinesulfonamide (0.82 mmol, 0.26 g) and triethylamine (1.80 mmol, 0.25 mL) in 10 mL .2 acetonitrile. The reaction mixture was warmed to 80° C. for 24 h. Then the reaction mixture was concentrated and purified via -standard flash chromotographic technique to give 1N-(4-morpholinesulfonamidophen-1-yl)aminocarbonylmethyl-6-cyanobenzoxazolinone. LRMS: m/z 460 (M+NH4). The 1N-(4- morpholinesulfonamidophen-1-yl) aminocarbonylmethyl-6- cyanobenzoxazolinone was converted to its corresponding benzamidine via the Pinner synthesis and amidination with ammonium carbonate to give the crude 1N-(4- morpholinesulfonamidophenyl) aminocarbonylmethyl-6- amidinobenzoxazolinone. The crude product was purified by standard reverse phase HPLC. $^1$H NMR (DMSO-d$_6$, 300 MHz): δ 11.10 (s, 1H), 9.21 (bs, 2H), 8.72 (bs, 2H), 7.91 (m, 3H), 7.82 (m, 4H), 4.53 (s, 2H), 3.62 (m, 4H), 2.88 (m, 4H). LRMS: m/z 460 (M+H). HRMS: calcd for C$_{21}$H$_{21}$N$_5$O$_6$S, 460.130418; found, 460.130002.

Example 101

3-(3-methoxy-(2'-aminosulfonyl-[1,1']biphenyl-1-aminocarbonyl)methyl-5-amidino-2-indolinone To a stirred solution of 3-(21-aminosulfonyl-(1,1']-biphenylaminocarbonyl)methyl-5-cyanoindole (300 mg, 0.62 mmol) in 10 mL of t-BuOH was added NBS (120 mg, 0.67 mmol) at rt and it stirred for 18 h. The reaction was diluted with water and extracted with ethyl acetate (3×), dried with sodium sulfate, filtered and concentrated in vacuo. The yellow residue was chromatographed via flash Silica Gel using 1:1 hexanes:ethylacetate as the eluant. Fractions were collected and concentrated in vacuo to afford of desired product in 35% yield (130 mg, 0.22 mmol). The bromo compound was then dissolved in dry MeOH cooled to –20° C. and saturated with HCl(g). Resulting solution was allowed to warm up to rt over 18 h. The reaction was concentrated in vacuo. The resulting residue was dissolved in dry MeOH and after addition of ammonium carbonate the flask sealed and stirred for 18 at rt. The mixture was filtered through Celite®, rinsed with MeOH, and methylene chloride. Concentration under vacuo afforded a mixture of products. Separation and purification was accomplished via prep. HPLC to afford the 3-methoxy, and the 3-amino 2-oxyindoles. $^1$H NMR (CD$_3$OD) δ ppm 3.05 (s, 3H), 3.25 (qd, 2H, J=15 Hz), 7.21(d,1H, J=7.5 Hz), 7.32 (m, 3H), 7.51 (m, 4H), 7.82 (d, J=7.5 Hz), 8.03, (m, 2H). HRMS (M+H)$^+$ for C$_{24}$H$_{24}$N$_5$O$_5$S calc: 494.149816; found: 494.149536.

Example 102

3-(3-amino-(2'aminosulfonyl-[1,1']-biphenylaminocarbonyl)methyl-5-amidino-2-indolinone Prepared and purified using the procedure from Example 101. $^1$H NMR (CD$_3$OD) δ ppm 3.25 (qd, 2H, J=15 Hz), 7.21(d,1H, J=7.5 Hz), 7.32 (m, 3H), 7.51 (m, 4H), 7.82 (d, J=7.5 Hz), 8.03, (m, 2H). HRMS (M+H)$^+$ for C$_{23}$H$_{23}$N$_6$O$_4$S calc: 479.148813; found: 479.149389.

Example 103

3-(3-hydroxy-(2'-aminosulfonyl-[1,1']-biphenylaminocarbonyl)methyl-5-amidino-2-indolinone Preparation of 3-(2'-aminosulfonyl-[1,1']-biphenylaminocarbonyl)methyl-5-cyanoindole.

To a stirred soluiton of 5-cyano-3-acetic acid indole (1.0 g, 50 mmol), BOP (3.32 g, 7.5 mmol) in DMF (35 mL) was added 4-(2-aminosulfonyl)phenyl-2-aminobenzene (1.48 mg, 6.0 mmol) and heated at 50° C. for 3 h. The reaction was diluted with water, extracted with ethyl acetate, washed with 10% HCl, sodium bicarbonate, brine, water, dried with magnesium sulfate, filtered and concentrated in vacuo to afford 420 mg of product. The t-butyl group was removed in TFA reflux for 1 h. Purified via silica gel using 100% ethyl acetate as the eluent to afford 530 mg of product. LRMS (M+H)$^+$ 431.

Preparation of 3-(2'-aminosulfonyl-[1,1']-biphenylaminocarbonyl)methyl-5-amidinoindole.

The 5-cyanoindole was subjected to the Pinner conditions followed by ammonium carbonate in dry MeOH. Purification was accomplished via prep HPLC to afford 264 mg of product. HRMS calc 448.14337; found 448.142583.

Preparation of 2-[3-(3-hydroxy-(2'-aminosulfonyl-[1,1']-biphenylaminocarbonyl)methyl]-5-amidino-2-indolinone.

To a stirred solution of 3-(21-aminosulfonyl-[1,1']-biphenylaminocarbonyl)methyl-5-amidinoindole (1.03 g, 2.1 mmol) in 30 mL of t-BuOH was added NBS (374 mg, 2.1 mmol) and stirred for 18 h at rt under a nitrogen atmosphere. The mixture was concentrated in vacuo and redissolved in dry MeOH/MeOAc (1:4) Ammonium carbonate (x's) was added the flask sealed and stirred at rt for 48 h. Resulting mixture was filtered through Celite®, rinsed with MeOH and methylene chloride and the filtrate was concentrated in vacuo. Purification was accomplished via prep HPLC to afford 60 mg of desired product as the TFA salt. $^1$H NMR (DMSO-d$_6$) δ ppm 3.05 (q, 2H, J=11.5 Hz), 6.98 (d, 1H, J=6.0 Hz) 7.18 (s, 2H), 7.22 (m, 3H), 7.41 (d, 1H, J=6.0 Hz), 7.40 (s, 1H), 7.58 (m, 2H), 7.75 (d, 1H, J=6.0 Hz), 7.82 (s, 1H), 8.0 (d, 1H, J=6.0 Hz)8.67 (bs, 2H), 9.15 (bs, 2H), 10.05 (bs, 1H), 10.78 (s, 1H). HRMS (M+H)$^+$ for C$_{23}$H$_{22}$N$_5$O$_5$S calc: 480.134166; found: 480.135777.

Example 104

3-(3'-hydroxy-(2-chioro-(2'-aminosulfonyl)-[1,1']-biphenylaninocarbonyl)methyl-5-amidino-2-indolinone Prepared using the procedure of Example 103. $^1$H NMR (CD$_3$OD) δ ppm 3.25 (qd, 2H, J=9 Hz), 7.04 (d, 1H, J=9 Hz), 7.23(m, 2H), 7.43 (nd, 1H, J=1.8 Hz), 7.58(m, 3H), 7.78(dd,1H, J=1.8 Hz, J=9.0 Hz), 7.83(nd, 1H, J=1.8 Hz), 8.04 (dd, 1H, J=1.8 Hz, J=9.0 Hz). HRMS (M+H)$^+$ for C$_{23}$H$_{21}$ClN$_5$O$_5$S calc.: 514.095194; found: 514.094336.

Example 105

3-(3'-amino-(2-chloro-(2'-aminosulfonyl)-[1,1']-biphenylaminocarbonyl)methyl-5-amidino-2-indolinone Isolated from the preparation of Example 104. $^1$H NMR (CD$_3$OD) δ ppm 3.05 (qd, 2H, J=9.0 Hz), 7.09 (d, 1H, J=6.0 Hz), 7.25 (t, 2H, J=6.0 Hz), 7.45 (m, 4H), 7.81 (d, 1H, J=6.0 Hz), 8.03 (m, 2H). HRMS (M+H)$^+$ for C$_{23}$H$_{21}$ClN$_6$O$_4$S calc.: 513.111178; found: 513.113281.

Example 201

3-(2-chloro-(2'-aminosulfonyl)-[1,1']biphenyl-3'-aminocarbonyl)methyl-5-amidino-2-indolinone Isolated from the preparation of Example 104. $^1$H NMR (CD$_3$OD) δ ppm 3.6 (s, 2H), 7.15 (d, 1H, J=7.2 Hz), 7.23 (d, 1H, J=4.8 Hz), 7.32 1H, J=4.8 Hz), 7.5 (m, 5H), 7.81 (d, 1H, J=7.2 Hz), 8.03 (s, 1H). HRMS (M+H)$^+$ for C$_{23}$H$_{19}$ClN$_5$O$_4$S calc.: 496.084629; found: 496.084051.

Example 202

3-(2-bromo-(21-aminosulfonyl)-[1,1']biphenyl-3'-aminocarbonyl)methyl-5-amidino-2-indolinone Prepared using the procedure of Example 201. $^1$H NMR (CD$_3$OD) δ ppm 3.58 (s, 2H), 7.12 (d, 1H, J=9.0 Hz), 7.21 (d, 1H, J=7.2 Hz), 7.36 (s, 2H), 7.58 (m,2H), 7.8 (d, 1H, J=9.0 Hz), 8.03 (d, 1H, J=7.2 Hz), 8.08 (s, 1H). HRMS (M+H)$^+$ for C$_{23}$H$_{19}$BrN$_5$O$_4$S calc.: 540.03442; found: 540.032207.

Example 203

3-(2-fluoro-(2'-aminosulfonyl)-[1,1']biphenyl-3'-aminocarbonyl)methyl-5-amidino-2-indolinone Prepared using the procedure of Example 201. $^1$H NMR (CD$_3$OD) δ ppm 3.58 (q, 2H, J=9.0 Hz), 7.04 (d, 1H, J=9.0 Hz), 7.16 (d, 1H, J=7.2 Hz), 7.21 (d, 1H, J=7.0 Hz), 7.23 (d, 1H, J=7.0 Hz), 7.58 (m, 3H), 7.81 (d, 1H, J=9.0Hz), 7.89 (s, 1H), 8.12 (m, 2H). HRMS (M+H)$^+$ for C$_{23}$H$_{19}$FN$_5$O$_4$S calc. : 480.114179; found: 480.114566.

Example 204

3-(2'-aminosulfonyl)-[1,1']biphenyl-3'-aminocarbonyl)methyl-5- amidino-2-indolinone Prepared using the procedure of Example 201. HRMS (M+H)$^+$ for C$_{23}$H$_{20}$FN$_5$O$_4$S calc.: 462.123601; found: 462.123950.

TABLE 1

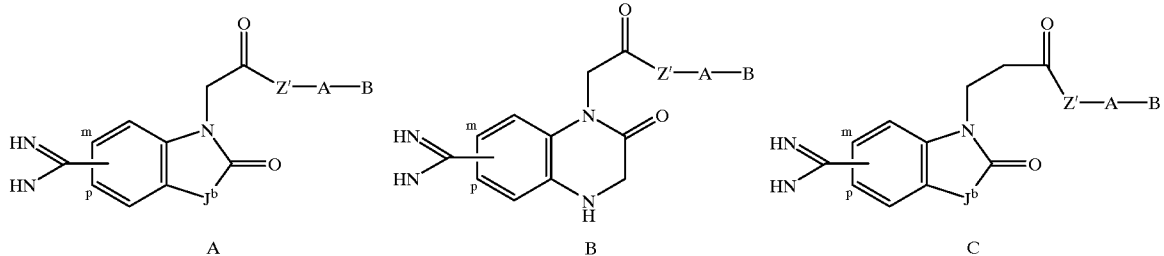

| Ex # | FIG. | Am | J$^b$ | Z'—A—B | MS |
|---|---|---|---|---|---|
| 1 | A | m | NH | 2'-aminosulfonyl-[1,1']-biphenylamino | 465.1345 |
| 2 | A | p | NH | 2'-aminosulfonyl-[1,1']-biphenylamino | 465.4 |
| 3 | A | m | NH | 4'-chlorophenyl-thiazol-2-yl | 427.0743 |
| 4 | A | p | NH | 4'-benzylpiperidino | 392.2071 |
| 5 | A | m | N—(CH$_2$)$_2$OH | 2'-aminosulfonyl-[1,1']-biphenylamino | 509.4 |
| 6 | A | m | O | 2'-aminosulfonyl-[1,1']-biphenylamino | 466.1157 |
| 7 | A | m | O | 4-(oxazol-5'-yl)phenylamino | 378 |
| 8 | A | m | O | 4'-(benzylsulfonyl)piperidino | 458.1516 |
| 9 | B | m | — | 4'-bromophenyl | 387.0286 |
| 10 | B | m | — | 2'-amino-[1,1']-biphenyl | 400.1780 |
| 11 | B | m | — | 4'-fluoro-[1,1']-biphenyl | 403 |
| 12 | B | m | — | [1,1']-biphenyl | 385.1650 |

TABLE 1-continued

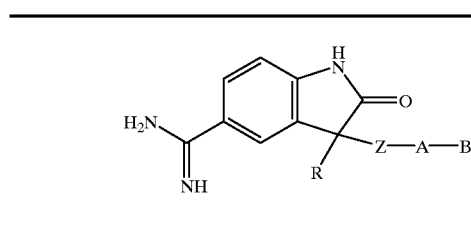

| Ex # | FIG. | Am | $J^b$ | Z'—A—B | MS |
|---|---|---|---|---|---|
| 13 | B | m | — | 2'-t-butylaminosulfonyl-[1,1']-biphenylamino | 520.2013 |
| 14 | B | m | — | 2'-aminosulfonyl-[1,1']-biphenylamino | 464.1396 |
| 15 | B | m | NH | 2'-aminosulfonyl-[1,1']-biphenylamino | 479.1491 |
| 16 | B | p | — | [1,1']-biphenyl | 385.1651 |
| 17 | C | m | O | [1,1']-biphenyl | 386 |
| 18 | C | m | NCH$_3$ | [1,1']-biphenyl | 399 |
| 19 | C | m | NH | [1,1']-biphenyl | 385 |
| 20 | C | m | O | 4-bromophenyl | 390 |
| 21 | A | m | O | 5-(2'-aminosulfonyl-phenyl)pyridin-2-ylamino | 467 |
| 22 | A | m | O | 4-(morpholinosulfonyl)phenylamino | 460 |

Unless otherwise defined, all stereochemistry is (+/−).

TABLE 2

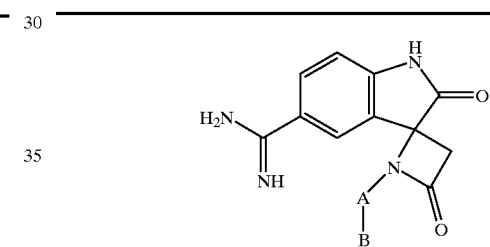

| Ex # | R | Z—A—B | MS |
|---|---|---|---|
| 101 | methoxy | 2'-aminosulfonyl-[1,1']-biphenyl-aminocarbonylmethyl | 494.1495 |
| 102 | amino | 2'-aminosulfonyl-[1,1']-biphenyl-aminocarbonylmethyl | 479.1488 |
| 103 | hydroxy | 2'-aminosulfonyl-[1,1']-biphenyl-aminocarbonylmethyl | 480.1358 |
| 104 | hydroxy | 2'-aminosulfonyl-2-chloro-[1,1']-biphenyl-aminocarbonylmethyl | 514.0943 |
| 105 | amino | 2'-aminosulfonyl-2-chloro-[1,1']-biphenyl-aminocarbonylmethyl | 513.1133 |

Unless otherwise defined, all stereochemistry is (+/−).

TABLE 3

| Ex # | A—B | MS |
|---|---|---|
| 201 | 2'-aminosulfonyl-2-chloro-[1,1']-biphenyl- | 496.0840 |
| 202 | 2'-aminosulfonyl-2-bromo-[1,1']-biphenyl- | 540.03221 |
| 203 | 2'-aminosulfonyl-2-fluoro-[1,1']-biphenyl- | 480.1146 |
| 204 | 2'-aminosulfonyl-2-[1,1']-biphenyl- | 462.1230 |

Unless otherwise defined, all stereochemistry is (+/−).

The following table contains representative examples of the present invention. Each entry in the table is intended to be paired with each formulae at the start of the table.

TABLE 4

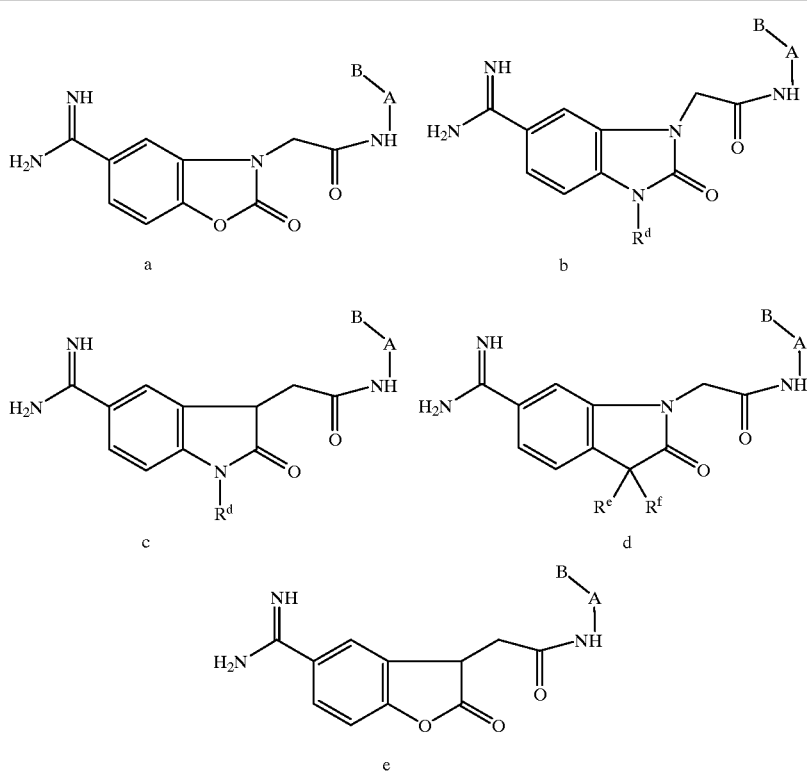

| Ex # | A | B |
| --- | --- | --- |
| 301 | phenyl | 2-(aminosulfonyl)phenyl |
| 302 | phenyl | 2-(methylaminosulfonyl)phenyl |
| 303 | phenyl | 1-pyrrolidinocarbonyl |
| 304 | phenyl | 2-(methylsulfonyl)phenyl |
| 305 | phenyl | 4-morpholino |
| 306 | phenyl | 2-(1'-CF$_3$-tetrazol-2-yl)phenyl |
| 307 | phenyl | 4-morpholinocarbonyl |
| 308 | 2-pyridyl | 2-(aminosulfonyl)phenyl |
| 309 | 2-pyridyl | 2-(methylaminosulfonyl)phenyl |
| 310 | 2-pyridyl | 1-pyrrolidinocarbonyl |
| 311 | 2-pyridyl | 2-(methylsulfonyl)phenyl |
| 312 | 2-pyridyl | 4-morpholino |
| 313 | 2-pyridyl | 2-(1'-CF$_3$-tetrazol-2-yl)phenyl |
| 314 | 2-pyridyl | 4-morpholinocarbonyl |
| 315 | 3-pyridyl | 2-(aminosulfonyl)phenyl |
| 316 | 3-pyridyl | 2-(methylaminosulfonyl)phenyl |
| 317 | 3-pyridyl | 1-pyrrolidinocarbonyl |
| 318 | 3-pyridyl | 2-(methylsulfonyl)phenyl |
| 319 | 3-pyridyl | 4-morpholino |
| 320 | 3-pyridyl | 2-(1'-CF$_3$-tetrazol-2-yl)phenyl |
| 321 | 3-pyridyl | 4-morpholinocarbonyl |
| 322 | 2-pyrimidyl | 2-(aminosulfonyl)phenyl |
| 323 | 2-pyrimidyl | 2-(methylaminosulfonyl)phenyl |
| 324 | 2-pyrimidyl | 1-pyrrolidinocarbonyl |
| 325 | 2-pyrimidyl | 2-(methylsulfonyl)phenyl |
| 326 | 2-pyrimidyl | 4-morpholino |
| 327 | 2-pyrimidyl | 2-(1'-CF$_3$-tetrazol-2-yl)phenyl |
| 328 | 2-pyrimidyl | 4-morpholinocarbonyl |
| 329 | 5-pyrimidyl | 2-(aminosulfonyl)phenyl |
| 330 | 5-pyrimidyl | 2-(methylaminosulfonyl)phenyl |
| 331 | 5-pyrimidyl | 1-pyrrolidinocarbonyl |
| 332 | 5-pyrimidyl | 2-(methylsulfonyl)phenyl |
| 333 | 5-pyrimidyl | 4-morpholino |
| 334 | 5-pyrimidyl | 2-(1'-CF$_3$-tetrazol-2-yl)phenyl |
| 335 | 5-pyrimidyl | 4-morpholinocarbonyl |
| 336 | 2-Cl-phenyl | 2-(aminosulfonyl)phenyl |
| 337 | 2-Cl-phenyl | 2-(methylaminosulfonyl)phenyl |
| 338 | 2-Cl-phenyl | 1-pyrrolidinocarbonyl |
| 339 | 2-Cl-phenyl | 2-(methylsulfonyl)phenyl |
| 340 | 2-Cl-phenyl | 4-morpholino |

TABLE 4-continued a b c d e

| Ex # | A | B |
|---|---|---|
| 341 | 2-Cl-phenyl | 2-(1'-CF$_3$-tetrazol-2-yl)phenyl |
| 342 | 2-Cl-phenyl | 4-morpholinocarbonyl |
| 343 | 2-F-phenyl | 2-(aminosulfonyl)phenyl |
| 344 | 2-F-phenyl | 2-(methylaminosulfonyl)phenyl |
| 345 | 2-F-phenyl | 1-pyrrolidinocarbonyl |
| 346 | 2-F-phenyl | 2-(methylsulfonyl)phenyl |
| 347 | 2-F-phenyl | 4-morpholino |
| 348 | 2-F-phenyl | 2-(1'-CF$_3$-tetrazol-2-yl)phenyl |
| 349 | 2-F-phenyl | 4-morpholinocarbonyl |
| 350 | 2,5-diF-phenyl | 2-(aminosulfonyl)phenyl |
| 351 | 2,5-diF-phenyl | 2-(methylaminosulfonyl)phenyl |
| 352 | 2,5-diF-phenyl | 1-pyrrolidinocarbonyl |
| 353 | 2,5-diF-phenyl | 2-(methylsulfonyl)phenyl |
| 354 | 2,5-diF-phenyl | 4-morpholino |
| 355 | 2,5-diF-phenyl | 2-(1'-CF$_3$-tetrazol-2-yl)phenyl |
| 356 | 2,5-diF-phenyl | 4-morpholinocarbonyl |

Unless otherwise defined, all stereochemistry is (+/−).

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, Km, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM-1 mm) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1 + S/K_m))$$

where:
- $v_o$ is the velocity of the control in the absence of inhibitor;
- $v_s$ is the velocity in the presence of inhibitor;
- I is the concentration of inhibitor;
- $K_i$ is the dissociation constant of the enzyme:inhibitor complex;
- S is the concentration of substrate;
- $K_m$ is the Michaelis constant.

Using the methodology described above, a number of compounds of the present invention were found to exhibit a $K_i$ of $\leq 15 \mu M$, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV- shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 15 $\mu m$, thereby confirming the utility of the compounds of the present invention as effective Xa inhibitors- The compounds of the present invention can be administered alone or in combination with one or more additional therapeutic agents. These include other anti- coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti- inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained- release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

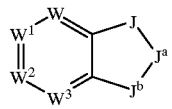

I or a stereoisomer or pharmaceutically acceptable salt thereof, wherein:
one of W, $W^1$, $W^2$, and $W^3$ is C—D and the remaining are C—$R^1$;
D is selected from CN, C(=$NR^7$)$NR^8R^9$, NHC(=$NR^7$)$NR^8R^9$, $NR^8$CH(=$NR^7$), C(O)$NR^8R^9$, and $(CH_2)_t$$NR^8R^9$;
Q is CO or CS;
R is selected from $C_{1-6}$ alkyl, $NH_2$, NH($C_{1-6}$ alkyl), N($C_{1-6}$ alkyl)$_2$, OH, $C_{1-6}$ alkoxy, $C_{1-6}$ alkoxy-$C_{1-4}$ alkyl, $(CH_2)_r$$NR^8R^9$, 5–6 membered aromatic heterocyclyl-$C_{1-4}$ alkyl, and aryl-$C_{1-4}$ alkyl, wherein the aromatic heterocyclyl and aryl groups are substituted with 0–1 $R^4$;
$R^a$ is selected from H, $C_{1-6}$ alkyl, C(O)$R^{2b}$, 5–6 membered aromatic heterocyclyl-$C_{1-4}$ alkyl, and aryl-$C_{1-4}$ alkyl, wherein the aromatic heterocyclyl and aryl groups are substituted with 0–1 $R^4$;
$R^b$ is H or $C_{1-2}$ alkyl;
$R^d$ is selected from H, OH, $NH_2$, $C_{1-2}$ alkyl, and $C_{1-2}$ alkyl-OH,
Z is selected from a bond, $C_{1-4}$ alkylene, $(CH_2)_rO(CH_2)_{r'}$, $(CH_2)_rNR^3(CH_2)_{r'}$, $(CH_2)_rC(O)(CH_2)_{r'}$, $(CH_2)_rC(O)O(CH_2)_{r'}$, $(CH_2)_rOC(O)(CH_2)_{r'}$, $(CH_2)_rC(O)NR^3(CH_2)_{r'}$, $(CH_2)_rNR^3C(O)(CH_2)_{r'}$, $(CH_2)_rOC(O)O(CH_2)_{r'}$, $(CH_2)_rOC(O)NR^3(CH_2)_{r'}$, $(CH_2)_rNR^3C(O)O(CH_2)_{r'}$, $(CH_2)_rNR^3C(O)NR^3(CH_2)_{r'}$, $(CH_2)_rS(O)_p(CH_2)_{r'}$, $(CH_2)_rSO_2NR^3(CH_2)_{r'}$, $(CH_2)_rNR^3SO_2(CH_2)_{r'}$, and $(CH_2)_rNR^3SO_2NR^3(CH_2)_{r'}$, provided that Z does not form a N—N, N—O, N—S, $NCH_2N$, $NCH_2O$, or $NCH_2S$ bond with the groups to which it is attached;

$R^1$, at each occurrence, is selected from H, F, Cl, Br, I, $(CF_2)_rCF_3$, $OR^2$, $NR^2R^{2a}$, $C(O)R^{2b}$, $(CF_2)_rCO_2R^2$, $S(O)_pR^{2b}$, $NR^2C(O)R^{2b}$, $C(O)NR^2R^{2a}$, $SO_2NR^2R^{2a}$, $C_{3-6}$ carbocyclic residue substituted with 0–2 $R^4$, and 5–10 membered heterocyclic system containing from 1–4 heteroatoms selected from the group consisting of N, O, and S and substituted with 0–2 $R^4$;

$R^{1'}$, at each occurrence, is selected from H, $C_{1-3}$ alkyl, F, Cl, Br, I, —CN, —CHO, $(CF_2)_rCF_3$, $(CH_2)_rOR^2$, $NR^2R^{2a}$, $C(O)R^{2c}$, $OC(O)R^2$, $(CF_2)_rCO_2R^{2c}$, $S(O)_pR^{2b}$, $NR^2(CH_2)_rOR^2$, CH(=$NR^{2c}$)$NR^2R^{2a}$, $NR^2C(O)R^{2b}$, $NR^2C(O)NHR^{2b}$, $NR^2C(O)_2R^{2a}$, $OC(O)NR^{2a}R^{2b}$, $C(O)NR^2R^{2a}$, $C(O)NR^2(CH_2)_rOR^2$, $SO_2NR^2R^{2a}$, $NR^2SO_2R^{2b}$, $C_{3-6}$ carbocyclic residue substituted with 0–2 $R^{4b}$, and 5–10 membered heterocyclic system containing from 1–4 heteroatoms selected from the group consisting of N, O, and S substituted with 0–2 $R^{4b}$;

$R^{1''}$, at each occurrence, is selected from H, CH($CH_2OR^2$)$_2$, $C(O)R^{2c}$, $C(O)NR^2R^{2a}$, $S(O)R^{2b}$, $S(O)_2R^{2b}$, and $SO_2NR^2R^{2a}$;

$R^2$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;

$R^{2a}$, at each occurrence, is selected from H, $CF_3$, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;

alternatively, $R^2$ and $R^{2a}$, together with the atom to which they are attached, combine to form a 5 or 6 membered saturated, partially saturated or unsaturated ring substituted with 0–2 $R^{4b}$ and containing from 0–1 additional heteroatoms selected from the group consisting of N, O, and S;

$R^{2b}$ is selected from $CF_3$, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S and substituted with 0–2 $R^{4b}$;

$R^{2c}$, at each occurrence, is selected from $CF_3$, OH, $C_{1-4}$ alkoxy, $C_{1-6}$ alkyl, benzyl, $C_{3-6}$ carbocyclic residue substituted with 0–2 $R^{4b}$, and 5–6 membered heterocyclic system containing from 1–4 heteroatoms selected from the group consisting of N, O, and S substituted with 0–2 $R^{4b}$;

$R^3$, at each occurrence, is selected from H, $C_{1-4}$ alkyl, and phenyl;

$R^{3a}$, at each occurrence, is selected from H, $C_{1-4}$ alkyl, and phenyl;

A is selected from:
$C_{3-10}$ carbocyclic residue substituted with 0–2 $R^4$, and 5–10 membered heterocyclic system containing from 1–4 heteroatoms selected from the group consisting of N, O, and S and substituted with 0–2 $R^4$;

B is selected from: Y and X—Y;
X is selected from $C_{1-4}$ alkylene, —$CR^2(CR^2R^{2b})$$(CH_2)_t$—, —C(O)—, —C(=$NR^{1''}$)—, —$CR^2$(NR$^{1''}R^2$)—, —$CR^2$(OR$^2$)—, —$CR^2$(SR$^2$)—, —C(O)

$CR^2R^{2a}$—, —$CR^2R^{2a}C(O)$, —$S(O)_p$—, —$S(O)_p$ $CR^2R^{2a}$—, —$CR^2R^{2a}S(O)_p$—, —$S(O)_2NR^2$—, —$NR^2S(O)_2$—, —$NR^2S(O)_2CR^2R^{2a}$—, —$CR^2R^{2a}S(O)_2NR^2$—, —$NR^2S(O)_2NR^2$—, —$C(O)NR^2$—, —$NR^2C(O)$—, —$C(O)NR^2CR^2R^{2a}$—, —$NR^2C(O)CR^2R^{2a}$—, —$CR^2R^{2a}C(O)NR^2$—, —$CR^2R^{2a}NR^2C(O)$—, —$NR^2C(O)O$—, —$OC(O)NR^2$—, —$NR^2C(O)NR^2$—, —$NR^2$—, —$NR^2CR^2R^{2a}$—, —$CR^2R^{2a}NR^2$—, O, —$CR^2R^{2a}O$—, and —$OCR^2R^{2a}$—;

Y is selected from:
$(CH_2)_rNR^2R^{2a}$, provided that X—Y do not form a N—N, O—N, or S—N bond, $C_{3-10}$ carbocyclic residue substituted with 0–2 $R^{4a}$, and 5–10 membered heterocyclic system containing from 1–4 heteroatoms selected from the group consisting of N, O, and S substituted with 0–2 $R^4$a; $R^4$, at each occurrence, is selected from H, =O, $(CH_2)_rOR^2$, F, Cl, Br, I, $C_{1-4}$ alkyl, —CN, $NO_2$, $(CH_2)_rNR^2R^{2a}$, $(CH_2)_rC(O)R^{2c}$, $NR^2C(O)R^{2b}$, $C(O)NR^2R^{2a}$, $NR^2C(O)NR^2R^{2a}$, $CH(=NR^2)NR^2R^{2a}$, $CH(=NS(O)_2R^5)$ $NR^2R^{2a}$, $NHC(=NR^2)NR^2R^{2a}$, $C(O)NHC(=NR^2)$ $NR^2R^{2a}$, $SO_2NR^2R^{2a}$, $NR^2SO_2NR^2R^{2a}$, $NR^2SO_2$—$C_{1-4}$ alkyl, $NR^2SO_2R^5$, $S(O)_pR^5$, $(CF_2)_rCF_3$, $NCH_2R^{1''}$, $OCH_2R^{1''}$, $SCH_2R^{1''}$, $N(CH_2)_2(CH_2)_rR^{1''}$, $O(CH_2)_2(CH_2)_rR^{1''}$, and $S(CH_2)_2(CH_2)_rR^{1''}$;

alternatively, one $R^4$ is a 5–6 membered aromatic heterocycle containing from 1–4 heteroatoms selected from the group consisting of N, O, and S;

$R^{4a}$, at each occurrence, is selected from H, =O, $(CH_2)_r$ $OR^2$, $(CH_2)_r$—F, $(CH_2)_r$—Br, $(CH_2)_r$—Cl, I, $C_{1-4}$ alkyl, —CN, $NO_2$, $(CH_2)_rNR^2R^{2a}$, $(CH_2)_rNR^2R^{2b}$, $(CH_2)_rC(O)R^{2c}$, $NR^2C(O)R^{2b}$, $C(O)NR^2R^{2a}$, $C(O)NH(CH_2)_2NR^2R^{2a}$, $NR^2C(O)NR^2R^{2a}$, $CH(=NR^2)$ $NR^2R^{2a}$, $NHC(=NR^2)NR^2R^{2a}$, $SO_2NR^2R^{2a}$, $NR^2SO_2NR^2R^{2a}$, $NR^2SO_2$—$C_{1-4}$ alkyl, $C(O)$ $NHSO_2$—$C_{1-4}$ alkyl, $NR^2SO_2R^5$, $S(O)_pR^5$, and $(CF_2)_r$ $CF_3$;

alternatively, one $R^{4a}$ is a 5–6 membered aromatic heterocycle containing from 1–4 heteroatoms selected from the group consisting of N, O, and S;

$R^{4b}$, at each occurrence, is selected from H, =O, $(CH_2)_r$ $OR^3$, F, Cl, Br, I, $C_{1-4}$ alkyl, —CN, $NO_2$, $(CH_2)_r$ $NR^3R^{3a}$, $(CH_2)_rC(O)R^3$, $(CH_2)_rC(O)OR^{3c}$, $NR^3C(O)$ $R^{3a}$, $C(O)NR^3R^{3a}$, $NR^3C(O)NR^3R^{3a}$, $CH(=NR^3)$ $NR^3R^{3a}$, $NH^3C(=NR^3)NR^3R^{3a}$, $SO_2NR^3R^{3a}$, $NR^3SO_2NR^3R^{3a}$, $NR^3SO_2$—$C_{1-4}$ alkyl, $NR^3SO_2CF_3$, $NR^3SO_2$-phenyl, $S(O)_pCF_3$, $S(O)_p$—$C_{1-4}$ alkyl, $S(O)_p$-phenyl, and $(CF_2)_rCF_3$;

$R^5$, at each occurrence, is selected from $CF_3$, $C_{1-6}$ alkyl, phenyl substituted with 0–2 $R^6$, and benzyl substituted with 0–2 $R^6$;

$R^6$, at each occurrence, is selected from H, OH, $(CH_2)_r$ $OR^2$, F, Cl, Br, I, $C_{1-4}$ alkyl, CN, $NO_2$, $(CH_2)_rNR^2R^{2a}$, $(CH_2)_rC(O)R^{2b}$, $NR^2C(O)R^{2b}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$, at each occurrence, is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$, at each occurrence, is selected from H, $C_{1-6}$ alkyl and $(CH_2)$n-phenyl;

$R^9$, at each occurrence, is selected from H, $C_{1-6}$ alkyl and $(CH_2)$n-phenyl;

p, at each occurrence, is selected from 0, 1, and 2;

r, at each occurrence, is selected from 0, 1, and 2; and, t, at each occurrence, is selected from 0 and 1;

provided that A—B is other than benzyl-thiazolidin-2,4-dione.

2. A compound according to claim 1, wherein; one of W, $W^1$, $W^2$, and $W^3$ is C—D and the remaining are C—$R^1$;

Q is CO;

Z is selected from a $CH_2O$, $OCH_2$, $CH_2NH$, $NHCH_2$, $CH_2C(O)$, $C(O)CH_2$, $C(O)NH$, $C(O)NH$, $CH_2S(O)_2$, $S(O)_2(CH_2)$, $SO_2NH$, and $SO_2NH$;

B is selected from: Y, X—Y, and $NR^2R^{2a}$;

Y is selected from one of the following carbocyclic and heterocyclic systems which are substituted with 0–2 $R^{4a}$;

phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, oxadiazole, thiadiazole, triazole, 1,2,3-oxadiazole, 1,2,4-oxadiazole, 1,2,5-oxadiazole, 1,3,4- oxadiazole, 1,2,3-thiadiazole, 1,2,4-thiadiazole, 1,2,5-thiadiazole, 1,3,4- thiadiazole, 1,2,3-triazole, 1,2,4-triazole, 1,2,5-triazole, 1,3,4-triazole, benzofuran, benzothiofuran, indole, benzimidazole, benzoxazole, benzthiazole, indazole, benzisoxazole, benzisothiazole, and isoindazole;

Y may also be selected from the following bicyclic heteroaryl ring systems:

K is selected from O, S, NH, and N.

3. A compound according to claim 2, wherein;

Ia or stereoisomer or pharmaceutically acceptable salt thereof, wherein;

D is $C(=NR^7)NR^8R^9$;

A is selected from:

piperidinyl,
piperazinyl,
$C_{5-6}$ carbocyclic residue substituted with 0–2 $R^4$, and
5–6 membered heteroaryl containing from 1–4 heteroatoms selected from the group consisting of N, O, and S and substituted with 0–2 $R^4$; and, B is selected from: Y and X—Y.

4. A compound according to claim 3, wherein;
Y is selected from one of the following carbocyclic and heterocyclic systems which are substituted with 0–2 $R^4a$;
  phenyl, piperidinyl, piperazinyl, pyridyl, pyrimidyl, furanyl, morpholinyl, thiophenyl, pyrrolyl, pyrrolidinyl, oxazolyl, isoxazolyl, thiazolyl, isothiazolyl, pyrazolyl, imidazolyl, benzimidazole, oxadiazole, thiadiazole, triazole, 1,2,3-oxadiazole, 1,2,4-oxadiazole, 1,2,5- oxadiazole, 1,3,4-oxadiazole, 1,2,3-thiadiazole, 1,2,4-thiadiazole, 1,2,5- thiadiazole, 1,3,4-thiadiazole, 1,2,3-triazole, 1,2,4-triazole, 1,2,5-triazole, and 1,3,4-triazole.

5. A compound according to claim 1, wherein the compound is selected from:
  2-[3-(3-methoxy-(2'-aminosulfonyl-[1,1']biphenyl-1-aminocarbonyl)methyl]-5- amidino-2-indolinone;
  2-[3-(3-amino-(2'-aminosulfonyl-[1,1']-biphenylaminocarbonyl)methyl]-5- amidino-2-indolinone;
  2-[3-(3-hydroxy-(2'-aminosulfonyl-[1,1']-biphenylaminocarbonyl)methyl]-5- amidino-2-indolinone;
  2-[3-(3'-hydroxy-(2-chloro-(2'-aminosulfonyl)-[1,1']-biphenylaminocarbonyl)methyl]-5-amidino-2-indolinone;
  2-[3-(3'-amino-(2-chloro-(2'-aminosulfonyl)-[1,1']-biphenylaminocarbonyl)methyl]-5-amidino-2-indolinone;
  2-(3-(2-chloro-(2'-aminosulfonyl)-[1,1']biphenyl-3'-aminocarbonyl)methyl)-5- amidino-2-indolinone;
  2-(3-(2-bromo-(2'-aminosulfonyl)-[1,1']biphenyl-3'-aminocarbonyl)methyl)-5- amidino-2-indolinone;
  2-(3-(2-fluoro-(2'-aminosulfonyl)-[1,1']biphenyl-3'-aminocarbonyl)methyl)-5- amidino-2-indolinone; and,
  2-(3-(2'-aminosulfonyl)-[1,1']biphenyl-3'-aminocarbonyl)methyl)-5-amidino-2- indolinone.

6. A pharmaceutical composition, comprising: a pharmaceutically acceptable carrier and a therapeutically effective amount of a compound according to claim 1 or a pharmaceutically acceptable salt thereof.

7. A pharmaceutical composition, comprising: a pharmaceutically acceptable carrier and a therapeutically effective amount of a compound according to claim 2 or a pharmaceutically acceptable salt thereof.

8. A pharmaceutical composition, comprising: a pharmaceutically acceptable carrier and a therapeutically effective amount of a compound according to claim 3 or a pharmaceutically acceptable salt thereof.

9. A pharmaceutical composition, comprising: a pharmaceutically acceptable carrier and a therapeutically effective amount of a compound according to claim 4 or a pharmaceutically acceptable salt thereof.

10. A pharmaceutical composition, comprising: a pharmaceutically acceptable carrier and a therapeutically effective amount of a compound according to claim 5 or a pharmaceutically acceptable salt thereof.

11. A method for treating a thromboembolic disorder, comprising: administering to a patient in need thereof a therapeutically effective amount of a compound according to claim 1 or a pharmaceutically acceptable salt thereof.

12. A method for treating a thromboembolic disorder, comprising: administering to a patient in need thereof a therapeutically effective amount of a compound according to claim 2 or a pharmaceutically acceptable salt thereof.

13. A method for treating a thromboembolic disorder, comprising: administering to a patient in need thereof a therapeutically effective amount of a compound according to claim 3 or a pharmaceutically acceptable salt thereof.

14. A method for treating a thromboembolic disorder, comprising: administering to a patient in need thereof a therapeutically effective amount of a compound according to claim 4 or a pharmaceutically acceptable salt thereof.

15. A method for treating a thromboembolic disorder, comprising: administering to a patient in need thereof a therapeutically effective amount of a compound according to claim 5 or a pharmaceutically acceptable salt thereof.

* * * * *

UNITED STATES PATENT AND TRADEMARK OFFICE
CERTIFICATE OF CORRECTION

PATENT NO. : 6,207,697 B1
DATED : March 27, 2001
INVENTOR(S) : Qi Han, Celia Dominquez, Eugene C. Amparo, Jeongsook M. Park, Mimi L. Quan and Karen A. Rossi It is certified that error appears in the above-identified patent and that said Letters Patent is hereby corrected as shown below:

Column 4,
Line 34, delete the "$(CF_2)_rCO_2R^2C$" and insert -- $(CF_2)_rCO_2R^{2c}$ --;

Column 5,
Line 19, delete the "$—NR^2S(O)2—$" and insert -- $—NR^2S(O)_2—$ --;
Line 59, delete the "$(CH_2)_rC(O)OR^3C$" and insert -- $(CH_2)_rC(O)OR^{3c}$ --;

Column 6,
Line 10, delete the "$C_{6-1}0$ arylcarbonyloxy" and insert -- $C_{6-10}$ arylcarbonyloxy --;

Column 7,
Line 63, delete the "$R^4a$" and insert -- $R^{4a}$ --;

Column 21,
Line 61, delete the "Pb(OAc)4" and insert -- $Pb(Oac)_4$ --;

Column 59,
Lines 47 and 48, insert -- J, $J^a$ and $J^b$ together are $CR(Z-A-B)(CR^aR^b)_aQNR^d$ --;

Column 61,
Line 16, delete the "$R^4a$" and insert -- $R^{4a}$ -- ;

Column 62,
Lines 2 and 3, insert -- a, at each occurrence, is selected from 0, 1, and 2; --;

UNITED STATES PATENT AND TRADEMARK OFFICE
CERTIFICATE OF CORRECTION

PATENT NO. : 6,207,697 B1
DATED : March 27, 2001
INVENTOR(S) : Qi Han, Celia Dominquez, Eugene C. Amparo, Jeongsook M. Park, Mimi L. Quan and Karen A. Rossi It is certified that error appears in the above-identified patent and that said Letters Patent is hereby corrected as shown below:

<u>Column 63,</u>
Line 11, delete the "$R^4a$" and insert -- $R^{4a}$ --.

Signed and Sealed this

Twenty-fifth Day of June, 2002

*Attest:*

*Attesting Officer*

JAMES E. ROGAN
*Director of the United States Patent and Trademark Office*